United States Patent
Hibner et al.

(10) Patent No.: US 9,414,814 B2
(45) Date of Patent: *Aug. 16, 2016

(54) BIOPSY DEVICE WITH ROTATABLE TISSUE SAMPLE HOLDER

(71) Applicant: Devicor Medical Products, Inc., Cincinnati, OH (US)

(72) Inventors: John A. Hibner, Mason, OH (US); Trevor W. V. Speeg, Williamsburg, OH (US); Bennie Thompson, Cincinnati, OH (US); Richard P. Nuchols, Williamsburg, OH (US); Wells D. Haberstich, Loveland, OH (US); Gavin M. Monson, Oxford, OH (US); Robert F. Weikel, Jr., Hamilton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,936

(22) Filed: Nov. 11, 2014

(65) Prior Publication Data

US 2015/0065914 A1    Mar. 5, 2015

Related U.S. Application Data

(63) Continuation of application No. 13/473,655, filed on May 17, 2012, now Pat. No. 8,905,943, which is a continuation of application No. 12/686,433, filed on Jan. 13, 2010, now Pat. No. 8,241,226, which is a (Continued)

(51) Int. Cl.
*A61B 10/00* (2006.01)
*A61B 10/02* (2006.01)

(52) U.S. Cl.
CPC ......... *A61B 10/0096* (2013.01); *A61B 10/0275* (2013.01); *A61B 10/0041* (2013.01); *A61B 10/0283* (2013.01); *A61B 2010/0225* (2013.01)

(58) Field of Classification Search
CPC .................. A61B 10/0275; A61B 10/0096
USPC .................. 600/562–568, 104; 235/375, 449, 235/462.01, 462.15; 141/133, 180, 35, 36, 141/94
See application file for complete search history.

(56) References Cited

U.S. PATENT DOCUMENTS

| 2,853,071 A | 9/1958 | Saffir |
| 3,630,192 A | 12/1971 | Jamshidi |

(Continued)

FOREIGN PATENT DOCUMENTS

| AU | 2008203258 A1 | 2/2009 |
| AU | 2008203259 A1 | 2/2009 |

(Continued)

OTHER PUBLICATIONS

EnCor MRI Specifications and Breast Biopsy System, SenoRx, 2005, pp. 102.

(Continued)

*Primary Examiner* — Adam J Eiseman
(74) *Attorney, Agent, or Firm* — Frost Brown Todd LLC

(57) ABSTRACT

A biopsy device comprises a probe body, a cannula extending distally from the probe body, a cutter moveable relative to the cannula to sever tissue, and a tissue sample holder coupled with the probe body. The tissue sample holder comprises a rotatable member having a plurality of recesses to receive tissue samples. The rotatable member can be operable to successively index each recess relative to a lumen defined by the cutter. A cover portion may be associated with the rotatable member and permits one or more recesses to be viewable through the cover. The recesses may be configured to carry one or more tissue samples as the rotatable member is rotated.

20 Claims, 29 Drawing Sheets

Related U.S. Application Data continuation of application No. 11/736,117, filed on Apr. 17, 2007, now Pat. No. 7,854,707, which is a continuation-in-part of application No. 11/198,558, filed on Aug. 5, 2005, now Pat. No. 7,867,173.

(60) Provisional application No. 60/874,792, filed on Dec. 13, 2006.

(56) References Cited

U.S. PATENT DOCUMENTS

| | | |
|---|---|---|
| 3,719,086 A | 3/1973 | Bannister et al. |
| 3,994,297 A | 11/1976 | Kopf |
| 4,051,852 A | 10/1977 | Villari |
| 4,600,014 A | 7/1986 | Beraha |
| 4,782,833 A | 11/1988 | Einhorn |
| 5,234,000 A | 8/1993 | Hakky et al. |
| 5,406,959 A | 4/1995 | Mann |
| 5,439,457 A | 8/1995 | Yoon |
| 5,526,822 A | 6/1996 | Burbank et al. |
| 5,532,168 A | 7/1996 | Marantz |
| 5,601,585 A | 2/1997 | Banik et al. |
| 5,645,209 A | 7/1997 | Green et al. |
| 5,649,547 A | 7/1997 | Ritchart et al. |
| 5,769,086 A | 6/1998 | Ritchart et al. |
| 5,775,333 A | 7/1998 | Burbank et al. |
| 5,873,967 A | 2/1999 | Clark et al. |
| 5,876,329 A | 3/1999 | Harhen |
| 5,928,164 A | 7/1999 | Burbank et al. |
| 5,964,716 A | 10/1999 | Gregoire et al. |
| 5,980,469 A | 11/1999 | Burbank et al. |
| 6,007,497 A | 12/1999 | Huitema |
| 6,017,316 A | 1/2000 | Ritchart et al. |
| 6,042,593 A | 3/2000 | Storz et al. |
| 6,077,230 A | 6/2000 | Gregoire et al. |
| 6,083,177 A | 7/2000 | Kobren et al. |
| 6,086,544 A | 7/2000 | Hibner et al. |
| 6,120,462 A | 9/2000 | Hibner et al. |
| 6,142,946 A | 11/2000 | Hwang et al. |
| 6,142,956 A * | 11/2000 | Kortenbach ........ A61B 10/0266 600/564 |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,402,701 B1 | 6/2002 | Kaplan et al. |
| 6,409,970 B1 | 6/2002 | Phifer |
| 6,428,486 B2 | 8/2002 | Ritchart et al. |
| 6,436,054 B1 | 8/2002 | Viola et al. |
| 6,485,436 B1 | 11/2002 | Truckai et al. |
| 6,488,636 B2 | 12/2002 | Bryan et al. |
| 6,527,731 B2 | 3/2003 | Weiss et al. |
| 6,544,194 B1 | 4/2003 | Kortenbach |
| 6,620,111 B2 | 9/2003 | Stephens et al. |
| 6,626,849 B2 | 9/2003 | Huitema et al. |
| 6,638,235 B2 | 10/2003 | Miller et al. |
| 6,659,338 B1 | 12/2003 | Dittmann et al. |
| 6,758,824 B1 | 7/2004 | Miller |
| 6,849,080 B2 | 2/2005 | Lee et al. |
| 6,986,748 B2 | 1/2006 | McAlister et al. |
| 7,025,098 B2 | 4/2006 | Osborne |
| 7,025,732 B2 | 4/2006 | Thompson et al. |
| 7,185,681 B2 | 3/2007 | Romano |
| 7,189,206 B2 | 3/2007 | Quick et al. |
| 7,204,811 B2 | 4/2007 | Kortenbach et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,278,991 B2 | 10/2007 | Morris et al. |
| 7,419,472 B2 | 9/2008 | Hibner et al. |
| 7,442,171 B2 | 10/2008 | Stephens et al. |
| 7,445,739 B2 | 11/2008 | Tsonton et al. |
| 7,470,237 B2 | 12/2008 | Beckman et al. |
| 7,497,833 B2 | 3/2009 | Miller |
| 7,517,321 B2 | 4/2009 | McCullough et al. |
| 7,556,622 B2 | 7/2009 | Mark et al. |
| 7,575,556 B2 | 8/2009 | Speeg et al. |
| 7,662,109 B2 | 2/2010 | Hibner |
| 7,740,594 B2 | 6/2010 | Hibner |
| 7,740,596 B2 | 6/2010 | Hibner |
| 7,740,597 B2 | 6/2010 | Cicenas et al. |
| 7,749,172 B2 | 7/2010 | Schwindt |
| 7,753,857 B2 | 7/2010 | Hibner |
| 7,758,515 B2 | 7/2010 | Hibner |
| 7,806,834 B2 | 10/2010 | Beckman et al. |
| 7,819,819 B2 | 10/2010 | Quick et al. |
| 7,828,745 B2 | 11/2010 | McAlister et al. |
| 7,828,748 B2 | 11/2010 | Hibner |
| 7,846,107 B2 | 12/2010 | Hoffman et al. |
| 7,854,706 B2 | 12/2010 | Hibner |
| 7,854,707 B2 * | 12/2010 | Hibner ............... A61B 10/0096 600/567 |
| 7,867,173 B2 | 1/2011 | Hibner et al. |
| 7,896,817 B2 | 3/2011 | Garrison |
| 7,918,804 B2 | 4/2011 | Monson et al. |
| 7,985,239 B2 | 7/2011 | Suzuki |
| 8,002,713 B2 | 8/2011 | Heske et al. |
| 8,016,772 B2 | 9/2011 | Heske et al. |
| 8,038,627 B2 | 10/2011 | Hibner |
| 8,118,755 B2 * | 2/2012 | Hibner ............... A61B 10/0275 600/562 |
| 8,177,728 B2 | 5/2012 | Hibner et al. |
| 8,177,729 B2 | 5/2012 | Hibner et al. |
| 8,206,316 B2 | 6/2012 | Hibner et al. |
| 8,235,913 B2 | 8/2012 | Hibner et al. |
| 8,241,226 B2 * | 8/2012 | Hibner ............... A61B 10/0096 600/567 |
| 8,262,586 B2 | 9/2012 | Almazan et al. |
| 8,568,335 B2 | 10/2013 | Monson et al. |
| 8,905,943 B2 * | 12/2014 | Hibner ............... A61B 10/0096 600/566 |
| 8,911,381 B2 | 12/2014 | Hibner et al. |
| 9,005,136 B2 | 4/2015 | Monson et al. |
| 2002/0076355 A1 | 6/2002 | Phifer |
| 2002/0120212 A1 | 8/2002 | Ritchart et al. |
| 2003/0125639 A1 | 7/2003 | Fisher et al. |
| 2003/0199753 A1 | 10/2003 | Hibner et al. |
| 2004/0068291 A1 * | 4/2004 | Suzuki ............... A61B 10/0096 606/205 |
| 2005/0049521 A1 | 3/2005 | Miller et al. |
| 2005/0065453 A1 | 3/2005 | Shabaz et al. |
| 2005/0215922 A1 | 9/2005 | Tsonton et al. |
| 2006/0041230 A1 | 2/2006 | Davis |
| 2006/0074344 A1 | 4/2006 | Hibner |
| 2006/0074345 A1 | 4/2006 | Hibner |
| 2006/0258955 A1 * | 11/2006 | Hoffman ............... A61B 10/06 600/564 |
| 2008/0004545 A1 | 1/2008 | Garrison |
| 2008/0082021 A1 | 4/2008 | Ichikawa et al. |
| 2008/0195066 A1 | 8/2008 | Speeg et al. |
| 2008/0214955 A1 | 9/2008 | Speeg et al. |
| 2010/0075664 A1 | 3/2010 | Maucksch |
| 2010/0106053 A1 | 4/2010 | Videbaek et al. |
| 2010/0152610 A1 | 6/2010 | Parihar et al. |
| 2010/0160816 A1 | 6/2010 | Parihar et al. |
| 2010/0160819 A1 | 6/2010 | Parihar et al. |
| 2010/0160824 A1 | 6/2010 | Parihar et al. |
| 2013/0150750 A1 | 6/2013 | Monson et al. |
| 2015/0141867 A1 | 5/2015 | Hibner et al. |

FOREIGN PATENT DOCUMENTS

| | | |
|---|---|---|
| CN | 1753646 A | 3/2006 |
| CN | 101237822 A | 8/2008 |
| CN | 101352357 A | 1/2009 |
| CN | 102846342 A | 1/2013 |
| EP | 0890339 | 1/1999 |
| EP | 0995400 | 4/2000 |
| EP | 1520518 | 4/2005 |
| EP | 1642533 | 4/2006 |
| EP | 1642534 A2 | 4/2006 |
| EP | 1832234 | 12/2007 |
| EP | 1932482 | 6/2008 |
| EP | 2022406 A2 | 2/2009 |

(56) References Cited

FOREIGN PATENT DOCUMENTS

| | | |
|---|---|---|
| EP | 2022407 A2 | 2/2009 |
| GB | 2018601 | 10/1979 |
| JP | H04-506010 A | 10/1992 |
| JP | H09-510638 A | 10/1997 |
| JP | H10-513384 A | 12/1998 |
| JP | H11-9605 A | 1/1999 |
| JP | 2000-279418 A | 10/2000 |
| JP | 2005-199044 A | 7/2005 |
| JP | 2006-509545 A | 3/2006 |
| JP | 2006-346179 A | 12/2006 |
| JP | 2009-505697 A | 2/2009 |
| JP | 2009-532081 A | 9/2009 |
| JP | 5437601 B2 | 3/2014 |
| JP | 5450999 B2 | 3/2014 |
| JP | 2014-087680 A | 5/2014 |
| JP | 5763158 B2 | 8/2015 |
| RU | 2021770 | 10/1994 |
| WO | WO 95/25465 A2 | 9/1995 |
| WO | WO 96/24289 A2 | 8/1996 |
| WO | WO 98/33436 | 8/1998 |
| WO | WO 99/20096 A2 | 4/1999 |
| WO | WO 00/30531 | 6/2000 |
| WO | WO 03/77768 | 9/2003 |
| WO | WO 2004/016177 | 2/2004 |
| WO | WO 2004/052179 | 5/2004 |
| WO | WO 2004/052212 | 6/2004 |
| WO | WO 2004/075728 | 9/2004 |
| WO | WO 2006/005342 | 1/2006 |
| WO | WO 2006/005344 A1 | 1/2006 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

Australian First Examination Report dated Mar. 2, 2015 for Application No. AU 201402113.
Australian Second Examination Report dated May 27, 2015 for Application No. AU 201402113.
Canadian Office Action dated Jul. 11, 2014 for Application No. CA 2,597,847.
European Search Report dated Dec. 1, 2005 for Application No. EP 05256035.
European Search Report dated Jun. 13, 2007 for Application No. EP 07250402.
European Communication dated Jun. 25, 2007 for Application No. EP 05256035.
European Search Report dated Nov. 14, 2007 for Application No. EP 07250926.
European Search Report dated Dec. 11, 2007 for Application No. EP 07253220.
European Communication dated Dec. 20, 2007 for Application No. EP 07253220.
European Examination Report dated May 13, 2008 for Application No. EP 07250402.
European Examination Report dated Mar. 19, 2009 for Application No. EP 07250926.
European Search Report dated Apr. 3, 2009 for Application No. 08252518.
European Search Report dated Apr. 3, 2009 for Application No. 08252524.
Supplemental European Search Report dated Dec. 16, 2009 for Application No. EP 06789155.
European Communication dated Apr. 26, 2010 for Application No. EP 08252524.
European Search Report dated Sep. 29, 2010 for Application No. EP 10251076.
Extended European Search Report dated Apr. 23, 2012 for Application No. EP 11193357.
European Communication dated Apr. 27, 2015 for Application No. EP 11193357.8.
Indian First Examination Report dated Jul. 31, 2014 for Application No. IN521/KOLNP/2008.
International Search Report dated Sep. 27, 2007 for Application No. PCT/US06/30022.
International Preliminart Report on Patentability dated Feb. 5, 2008 for Application No. PCT/US2006/030022.
International Search Report dated Dec. 18, 2008 for Application No. PCT/US2008/058627.
Japanese Office Action dated May 26, 2015 for Application No. JP 2013-268757.
US Non-Final Office Action dated Mar. 20, 2008 for U.S. Appl. No. 11/782,963.
US Non-Final Office Action dated Apr. 4, 2008 for U.S. Appl. No. 11/736,117.
US Final Office Action dated Sep. 26, 2008 for U.S. Appl. No. 11/782,963.
US Non-Final Office Action dated Oct. 6, 2008 for U.S. Appl. No. 11/736,117.
US Reissue U.S. Appl. No. 13/507,652, filed Jul. 16, 2012.
US Reissue U.S. Appl. No. 13/672,037, filed Nov. 8, 2012.
US Provisional U.S. Appl. No. 60/869,736, filed Dec. 13, 2006.
US Provisional U.S. Appl. No. 60/874,792, filed Dec. 13, 2006.
Australian Office Action dated Aug. 27, 2012 for Application No. AU 2008203259, 3 pgs.
Australian Office Action dated Feb. 23, 2013 for Application No. AU 2008203258, 3 pgs.
Australian Office Action dated Jul. 3, 2014 for Application No. AU 2013205332, 6 pgs.
Canadian Office Action dated Jan. 29, 2015 for Application No. CA 2,638,237, 4 pgs.
Chinese Office Action dated Mar. 25, 2011 for Application No. CN 200810214771.5, 11 pgs.
Chinese Office Action dated Apr. 19, 2011 for Application No. CN 200810144042.7, 9 pgs.
Chinese Office Action dated Mar. 28, 2012 for Application No. CN 200810144042.7, 6 pgs.
Chinese Office Action dated Jan. 20, 2014 for Application No. CN 201210348968.4, 7 pgs.
Japanese Office Action dated Apr. 9, 2013 for Application No. JP 2008-190428, 4 pgs.
Japanese Office Action dated Apr. 23, 2013 for Application No. JP 2008-190430, 4 pgs.
Japanese Office Action dated Sep. 30, 2014 for Application No. JP 2013-268757, 2 pgs.
Japanese Office Action dated Oct. 7, 2014 for Application No. JP 2013-255839, 3 pgs.

* cited by examiner

BIOPSY DEVICE WITH ROTATABLE TISSUE SAMPLE HOLDER

CROSS REFERENCE TO RELATED APPLICATIONS

The present application is a continuation of commonly-owned U.S. patent application Ser. No. 13/473,655, entitled "BIOPSY DEVICE WITH ROTATABLE TISSUE SAMPLE HOLDER," filed on May 17, 2012, published as U.S. Pat. Pub. No. 2012/0226193 on Sep. 6, 2012, which is a continuation of U.S. patent application Ser. No. 12/686,433, entitled "BIOPSY DEVICE WITH ROTATABLE TISSUE SAMPLE HOLDER," filed Jan. 13, 2010, issued as U.S. Pat. No. 8,241,226 on Aug. 14, 2012, which is a continuation of U.S. patent application Ser. No. 11/736,117, entitled "TISSUE SAMPLE REVOLVER DRUM BIOPSY DEVICE," filed Apr. 17, 2007, issued as U.S. Pat. No. 7,854,707 on Dec. 21, 2010, the disclosures of which are hereby incorporated by reference in their entirety.

U.S. patent application Ser. No. 11/736,117 is a continuation-in-part of commonly-owned U.S. patent application Ser. No. 11/198,558, entitled "BIOPSY DEVICE WITH REPLACEABLE PROBE AND INCORPORATING VIBRATION INSERTION ASSIST AND STATIC VACUUM SOURCE SAMPLE STACKING RETRIEVAL," filed Aug. 5, 2005, issued as U.S. Pat. No. 7,867,173 on Jan. 11, 2011, the disclosure of which is hereby incorporated by reference in its entirety.

U.S. patent application Ser. No. 11/736,117 also claims priority to U.S. Pat. Appln. Ser. No. 60/874,792, entitled "BIOPSY SAMPLE STORAGE" to Hibner et al., filed Dec. 13, 2006, the disclosure of which is hereby incorporated by reference in its entirety.

FIELD OF THE INVENTION

The present invention relates in general to biopsy devices, and more particularly to biopsy devices having a cutter for severing tissue, and even more particularly to biopsy devices for multiple sampling with a probe remaining inserted.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the trade name MAMMOTOME is commercially available from DEVICOR MEDICAL PRODUCTS, INC. for use in obtaining breast biopsy samples. This device generally retrieves multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned patents and patent applications: U.S. Pat. No. 7,419,472, entitled "Biopsy Instrument with Internal Specimen Collection Mechanism," issued Sep. 2, 2008 in the name of Hibner et al.; and U.S. Pat. No. 7,740,597, entitled "Biopsy Device with Sample Tube," issued Jun. 22, 2010 in the name of Cicenas et al. The cutter is cycled across the side aperture, reducing the sample time. Several alternative specimen collection mechanisms are described that draw samples through the cutter tube, all of which allow for taking multiple samples without removing the probe from the breast.

In particular, in the cross referenced U.S. Pat. Pub. No. 2006/0074345, entitled "BIOPSY APPARATUS AND METHOD", these tissue samples are drawn by vacuum proximally through the cutter tube into a serial tissue stacking assembly that preserves the order of sample taking, can be visually observed through a transparent lumen, and can serve as a transport container for samples taken during a pathology examination.

While these known tissue storage approaches have a number of advantages, it is believed that further improvements may be made in tissue storage and transport for core biopsy procedures.

SUMMARY OF THE INVENTION

The present invention addresses these and other problems of the prior art by providing a biopsy device that has a probe cannula that is inserted into tissue to obtain a core biopsy sample by translating a cutter with the probe cannula. A pneumatic pressure differential is used to draw a severed tissue sample proximally from the probe cannula into an individual sample container. Thereafter, another empty sample container is moved into position to accept the next tissue sample.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
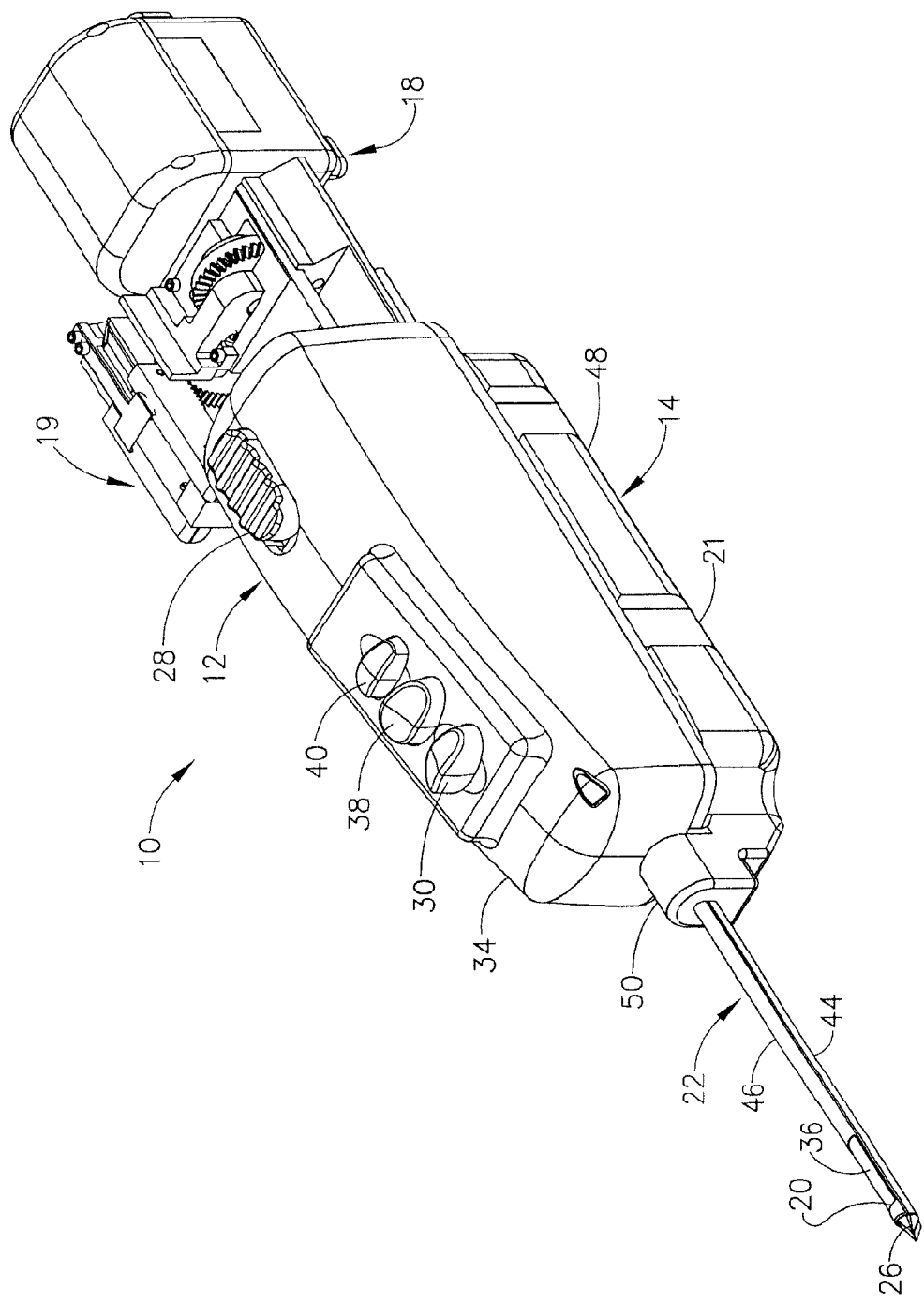
FIG. 1 is an isometric view of a biopsy device with an attached sample revolver drum assembly consistent with the present invention.
Figure 2:
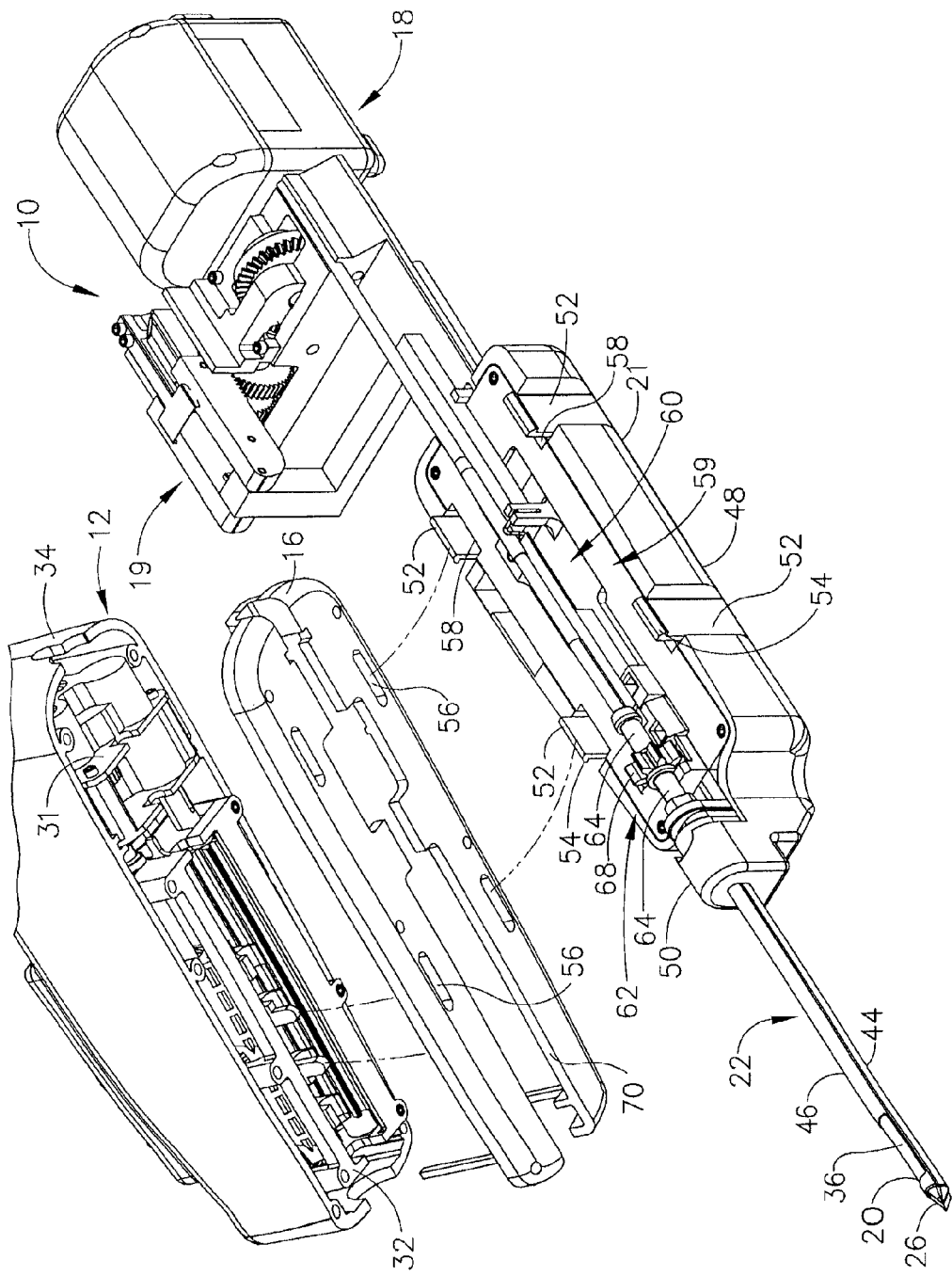
FIG. 2 is an isometric view of the biopsy device of FIG. 1 with a disposable probe assembly that includes the sample revolver drum assembly disengaged from a reusable handpiece that has a lower tray removed to expose a carriage frame assembly and a motor drive assembly.

Turning to the Drawings, wherein like numerals denote like components throughout the several views, in FIGS. 1-2, a biopsy device 10 includes a reusable handpiece 12, and a disposable probe assembly 14. A lower handle tray 16 is disassembled from upper portions of the reusable handpiece 12 to expose portions that operably engage the disposable probe assembly 14. A sample revolver drum assembly 18 is prepared to receive the next tissue sample by an indexing assembly 19 attached to a hand-held distal portion 21 of the disposable probe assembly 14 that mounts to and is actuated by the reusable handpiece 12. Tissue that is drawn by vacuum assistance into a side aperture 20 of a probe cannula 22 of the disposable probe assembly 14 is severed by a DC motor 24 (FIG. 3) in the reusable handpiece 12 that also powers rotation and staging of the sample revolver drum assembly 18 to segregate and store the tissue samples in the order received.

Figure 3:
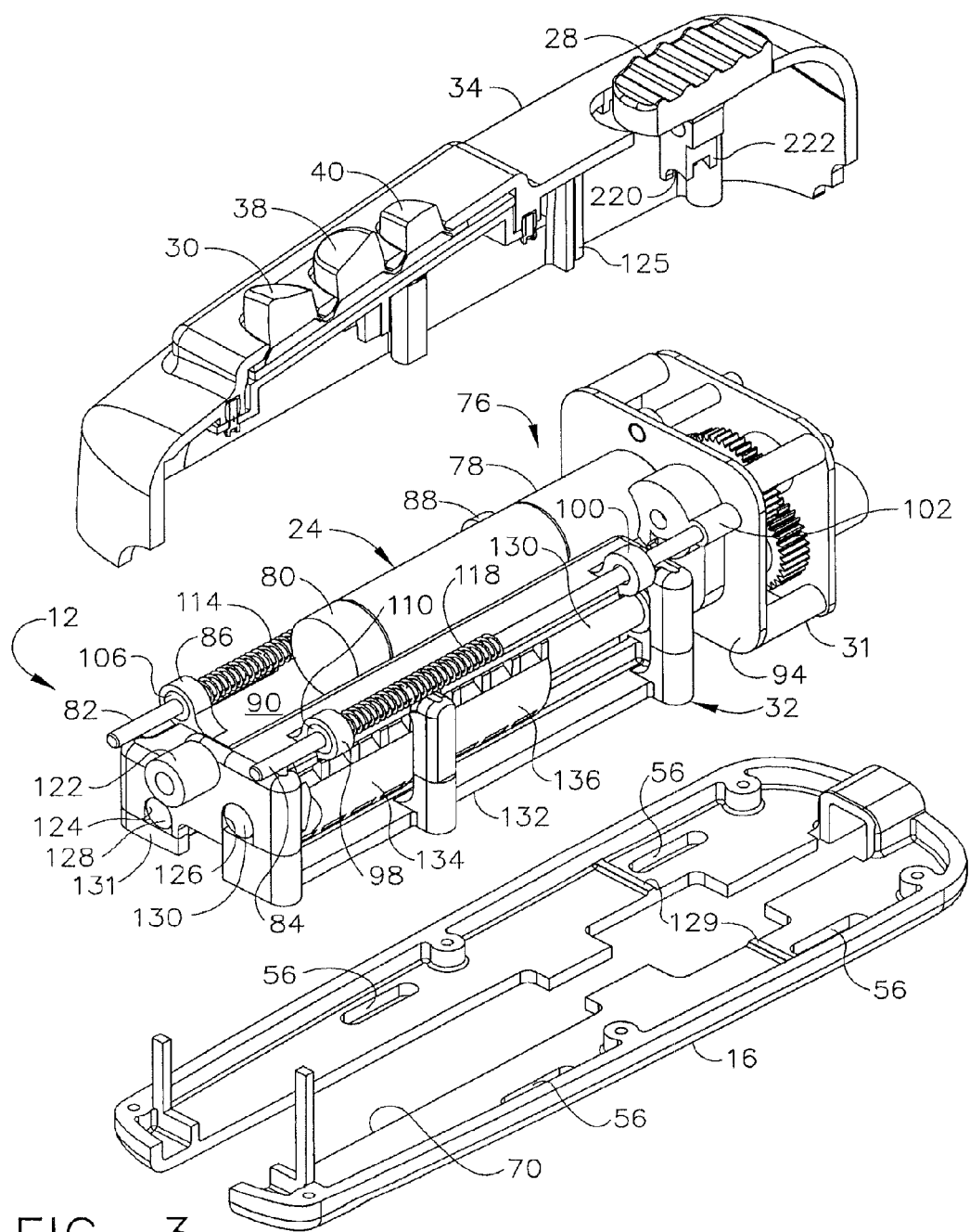
FIG. 3 is an isometric view of the reusable handpiece of FIG. 1 with a top cover detached with a left half cut away and with the lower handle tray detached to expose the motor drive assembly operatively engaged to the carriage frame assembly.

With particular reference to FIG. 1, insertion of the probe cannula 22 into tissue is integrally supported by a piercing tip 26 attached at a distal end as well as a longitudinal jack hammer motion to the probe cannula 22 selected by positioning a slide button 28 distally and depressing a forward motor button 30. In response, the DC motor 24 drives a transmission section 31 (FIG. 2) grounded to a top cover 34 of the reusable handpiece 12 to longitudinally reciprocate an internal carriage frame assembly 32 (FIG. 2) that is engaged for movement with the probe cannula 22 (FIG. 3). With the slide button 28 proximally positioned, depression of the forward motor button 30 causes the DC motor 24 to advance and rotate a cutter tube 36, depicted in FIG. 1 as having been fully distally translated, closing the side aperture 20. Depression of a reverse motor button 38 causes the cutter tube 36 to retract. Depression of a mode button 40 may cause other functions to be performed. An external conduit 42 extends from the disposable probe assembly 14 and is terminated by a filter/tube fitting 43. Vacuum assistance passes through a lateral lumen 44 of the probe cannula 22 and distally communicates via internal vent holes 47 (FIG. 23) and then enters a cutter lumen 46 that encompasses the cutter tube 36 and includes the side aperture 20. An additional feature contemplated but not depicted includes using the mode button 40 to selectively communicate a saline supply to lateral lumen 44 to flush the probe cannula. It should be appreciated that the biopsy device 10 includes a minimum of "tethers" that would impede use, pose a tripping hazard, or extend set-up time.

Alternatively, instead of "hard-walled" lateral lumen 44 separated from the cutter lumen 46 along its length, applications consistent with the present invention may have a cylindrical probe cannula wherein the cutter tube 36 is positioned off-center to translate across a side aperture. A "soft-walled" lateral lumen may then be defined as a space between an outer diameter of the cutter tube and an inner diameter of the cylindrical probe cannula.

In FIG. 2, the disposable probe assembly 14 has a bottom cover 48 with a distal probe mount cover 50 that assists in supporting the probe cannula 22 while allowing the longitudinal jack hammer motion. A plurality of locking tabs 52 with locking edges 54 extend upwardly through pass-through slots 56 formed in the periphery of the lower handle tray 16 to resiliently extend outwardly into engaging contact with the slots 56. Relieved areas 58 are formed behind each locking tab 52 in a top extension member 59 that surrounds a probe support body 60. The combination covers a cavity defined by the bottom cover 48, which allows depression of the locking tabs 52 to unlock the disposable probe assembly 14 to install another identical or similar assembly.

A proximal end of the cutter tube 36 receives a cutter gear 62 having distal and proximal reduced diameter bearing surfaces 64, 66 on each longitudinal side of a rotation spur gear section 68, which engage the reusable handpiece 12 for rotation and for longitudinal translation through a distally open longitudinal aperture 70 formed in the lower handle tray 16.

Figure 4:
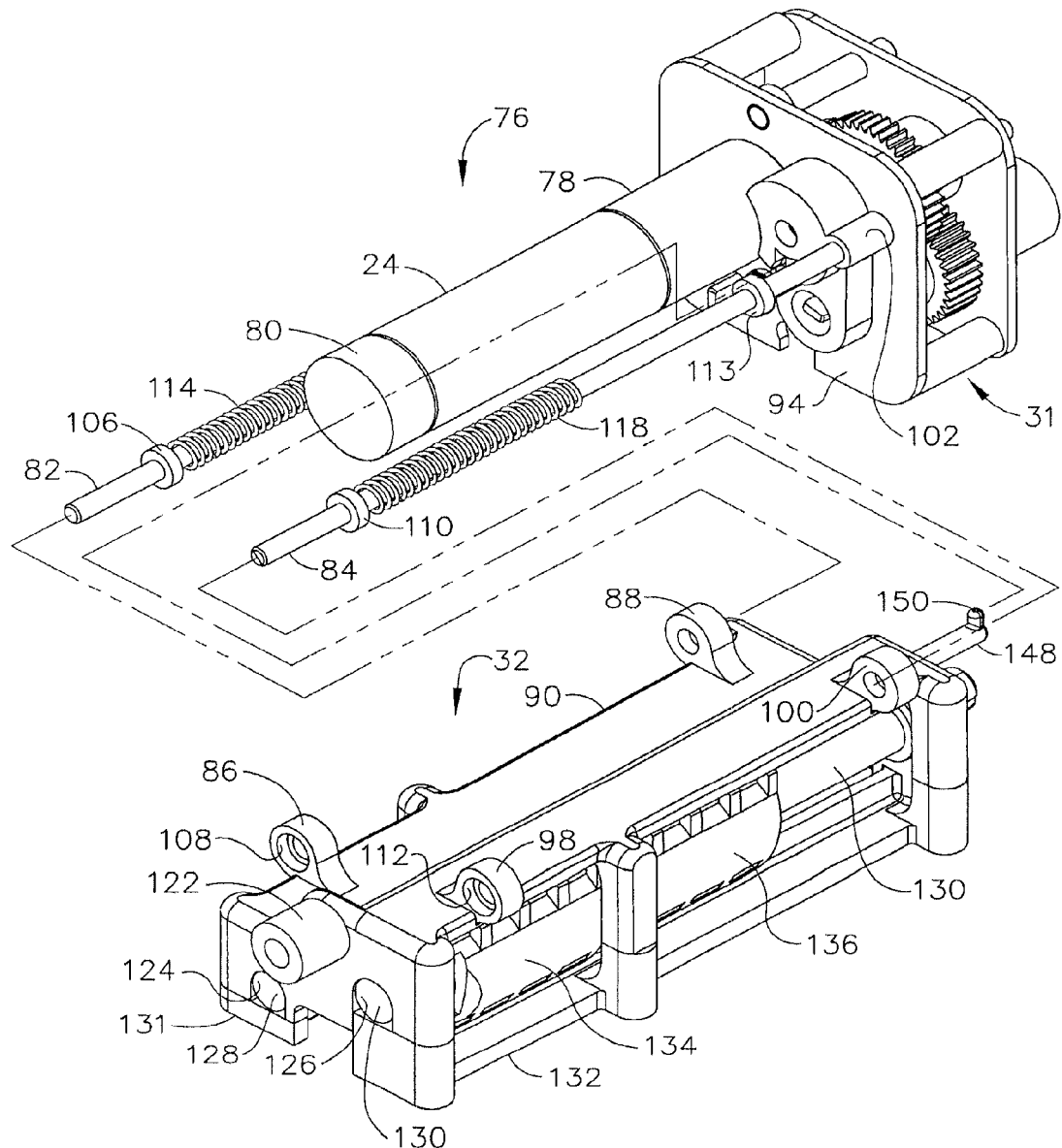
FIG. 4 is an isometric view of the motor drive assembly removed from the carriage frame assembly of FIG. 3.

REUSABLE HANDPIECE. In FIGS. 3-13, the reusable handpiece 12 is depicted in various states of disassembly to illustrate its operation. The transmission section 31 is part of a rigidly mounted motor drive assembly 76 that includes the motor 24 in between a planetary gearbox 78 and an encoder 80. The battery or other power source and control circuitry are omitted in the depictions. The motor drive assembly also includes a right guide pin 82 and a left guide pin 84. The motor drive assembly 76 is shown operably engaged to the longitudinally reciprocating carriage frame assembly 32 in FIG. 3 and is disassembled from the longitudinally reciprocating carriage frame assembly in FIG. 4. In FIG. 4, the right guide pin 82 is inserted proximally through a right front pin guide 86 and then through a right rear pin guide 88, both part of an upper frame 90 of the carriage frame assembly 32. A proximal end of the right guide pin 82 resides within a distally projecting right pin receptacle 92 (FIG. 12) formed as part of a distal bulkhead 94 of the transmission section 31. A distal end of the right guide pin 82 is received by a right pin recess 96 (FIG. 5) formed in the top cover 34. Similarly, the left guide pin 84 is inserted proximally through a left front pin guide 98 and then through a left rear pin guide 100, both part of the upper frame 90 of the carriage frame assembly 32. A proximal end of the left guide pin 84 resides within a distally projecting left pin receptacle 102, respectively formed as part of the distal bulkhead 94 of the transmission section 31. A distal end of the left guide pin 84 is received by a left pin recess 104 (FIG. 5) formed in the top cover 34.

With particular reference to FIGS. 3, 4, 6, 7 and 12, a right front ring bearing 106 is inserted over a distal portion of the right guide pin 82 and is received within a cylindrical recess 108 formed on a distal side of the right front pin guide 86. A right aft ring bearing 109 is inserted over a proximal portion of the right guide pin 82 and is received within a cylindrical recess 111 (FIG. 6) formed on a proximal side of the right aft pin guide 88. A left front ring bearing 110 is inserted over a distal portion of the left guide pin 84 and is received within a cylindrical recess 112 formed on a distal side of the left front pin guide 98. A left aft ring bearing 113 (FIG. 9) is inserted over a proximal portion of the left guide pin 84 and is received within a left cylindrical recess 115 (FIG. 6) formed on a proximal side of the left rear pin guide 100 A right compression spring 114 is proximally received over the right guide pin 82 between the right front and rear pin guides 86, 88. More particularly, the right compression spring 114 is distally positioned against the right front pin guide 86 and at its proximal end by a right downwardly projecting structure 116 (FIG. 5) formed on an interior of the top cover 34 that closely encompasses a top portion of the right guide pin 82 without contacting other portions of the carriage frame assembly 32. A left compression spring 118 is proximally received over the left guide pin 84 between the left front and rear pin guides 98, 100. More particularly, the left compression spring 118 is distally positioned against the left front pin guide 98 at its distal end by a left downwardly projecting structure 120 (FIG. 5) formed on the interior of the top cover 34 that closely encompasses a top portion of the left guide pin 84 without contacting other portions of the carriage frame assembly 32. Thereby, the carriage frame assembly 32 is biased to a distal position relative to the top cover 34 and lower handle tray 16.

Figure 5:
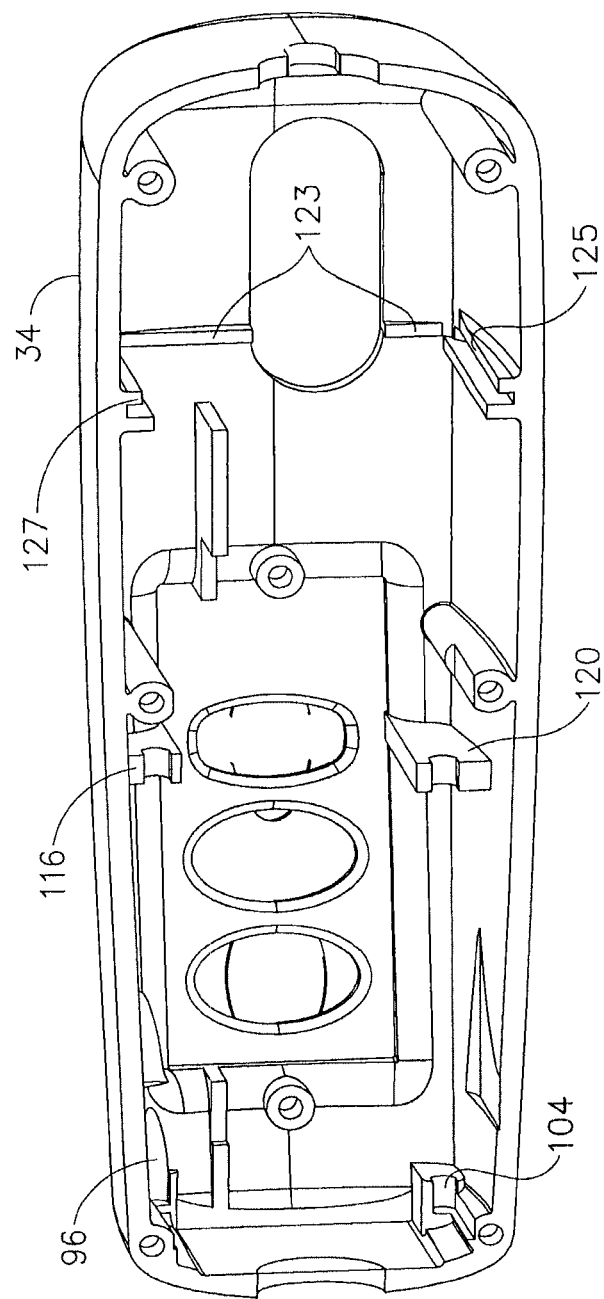
FIG. 5 is a bottom isometric view of the top cover of the reusable handpiece of FIG. 2.

In FIGS. 3-5, a forward projecting cylindrical resilient member 122 fastened to the upper frame 90 reduces noise by contacting the front interior of the top cover 34 slowing distal movement of the carriage frame assembly 32 prior to reaching full travel. The distal bulkhead 94 is restrained by being proximal to a top ridge 123, a right ridge 125, and a left ridge 127 (FIG. 5) formed in the interior of the top cover 34 and to a bottom ridge 129 formed on an upper surface of the lower handle tray 16.

Figure 6:
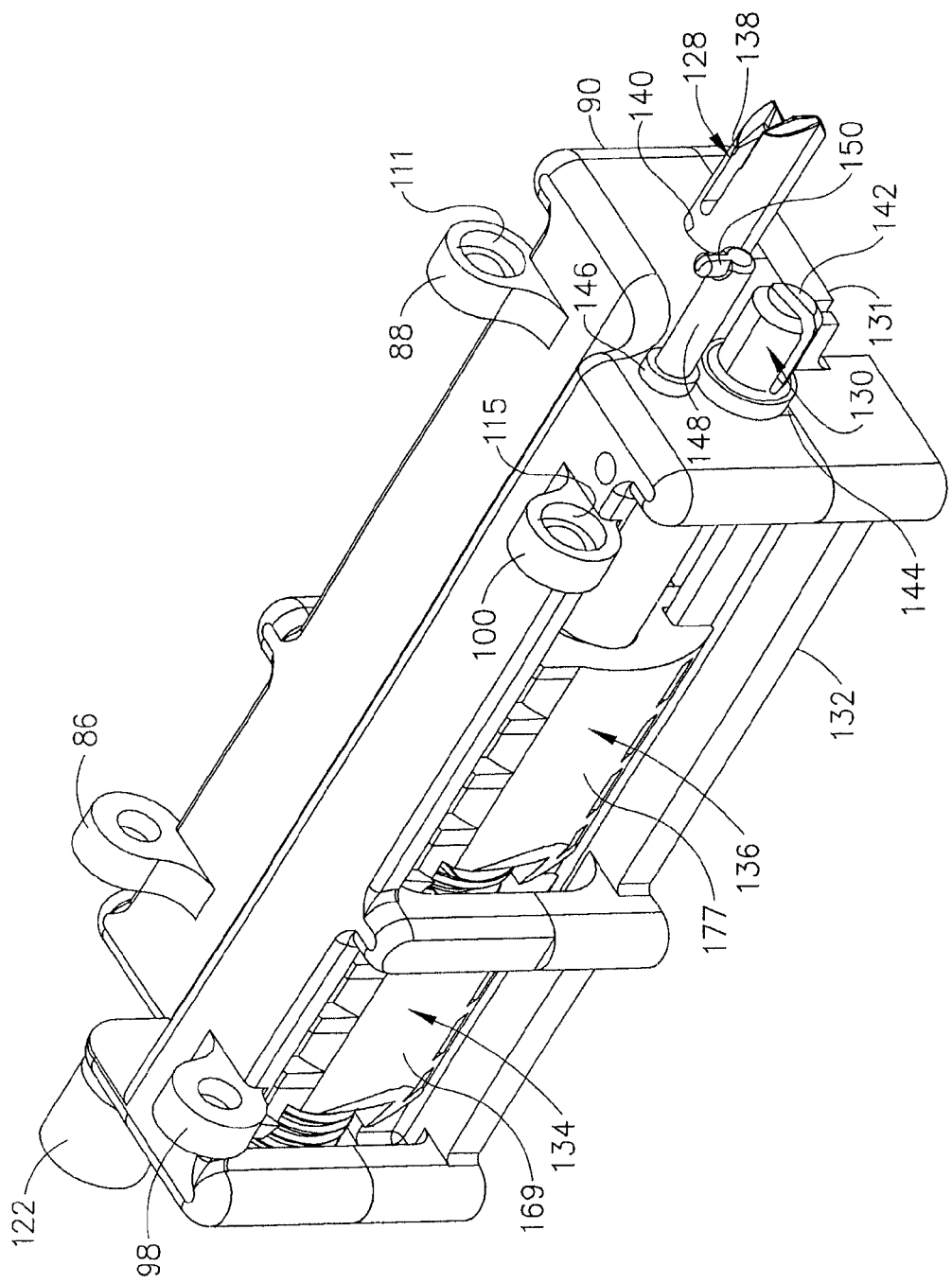
FIG. 6 is a top, left and aft isometric view of the carriage frame assembly of FIG. 4.
Figure 7:
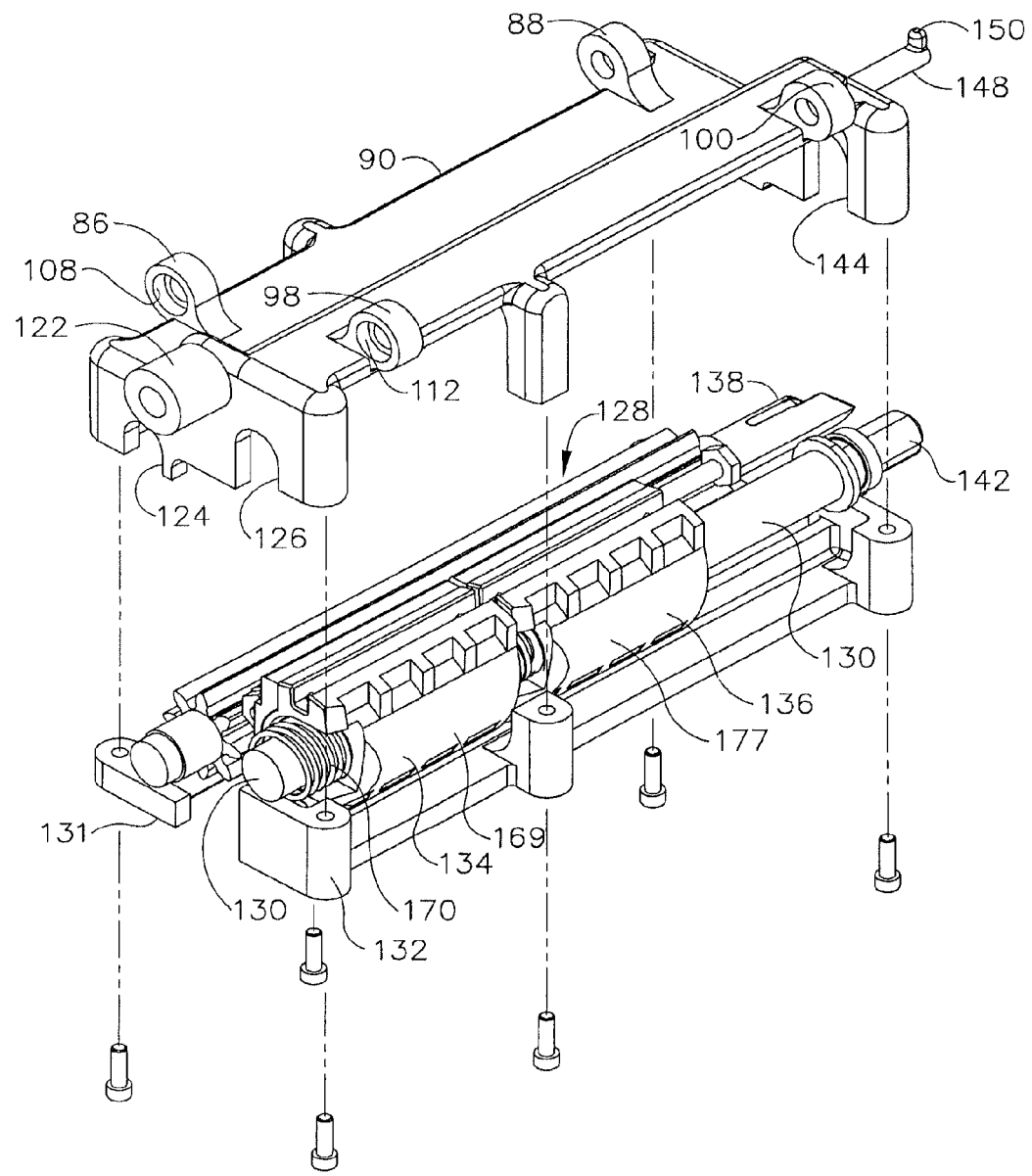
FIG. 7 is a top, left and forward view of the carriage frame assembly of FIG. 4 with an upper frame disassembled.

Returning to FIGS. 3-4 and 7, the upper frame 90 has right and left front shaft apertures 124, 126 that respectfully receive for rotation a distal end of a rotation shaft 128 and a translation shaft 130. The right front shaft aperture 124 is closed by the front portion of a right lower frame 131 of the carriage frame assembly 32. The left front shaft aperture 126 is closed by the front portion of a left lower frame 132 of the carriage frame assembly 32. A front (cutter) carriage 134 and an aft (straw) carriage 136 are received on the translation shaft 130 and are encompassed by the upper and lower frames 90, 132. In FIG. 6, a proximal beveled and slotted end 138 of the rotation shaft 128 extends out of right aft shaft aperture 140 formed in the upper frame 90 for engagement to the transmission section 31 and is closed by an aft portion of the right lower frame 131. A proximal slotted end 142 of the translation shaft 130 extends out of a left aft aperture 144 formed in the upper frame 90 for engagement to the transmission section 31 and is closed by the lower frame 132. A threaded receptacle 146 on the aft end of the upper frame 90 receives a proximally projecting bolt 148 having an upwardly directed strike pin 148 at its proximal end.

Figure 8:
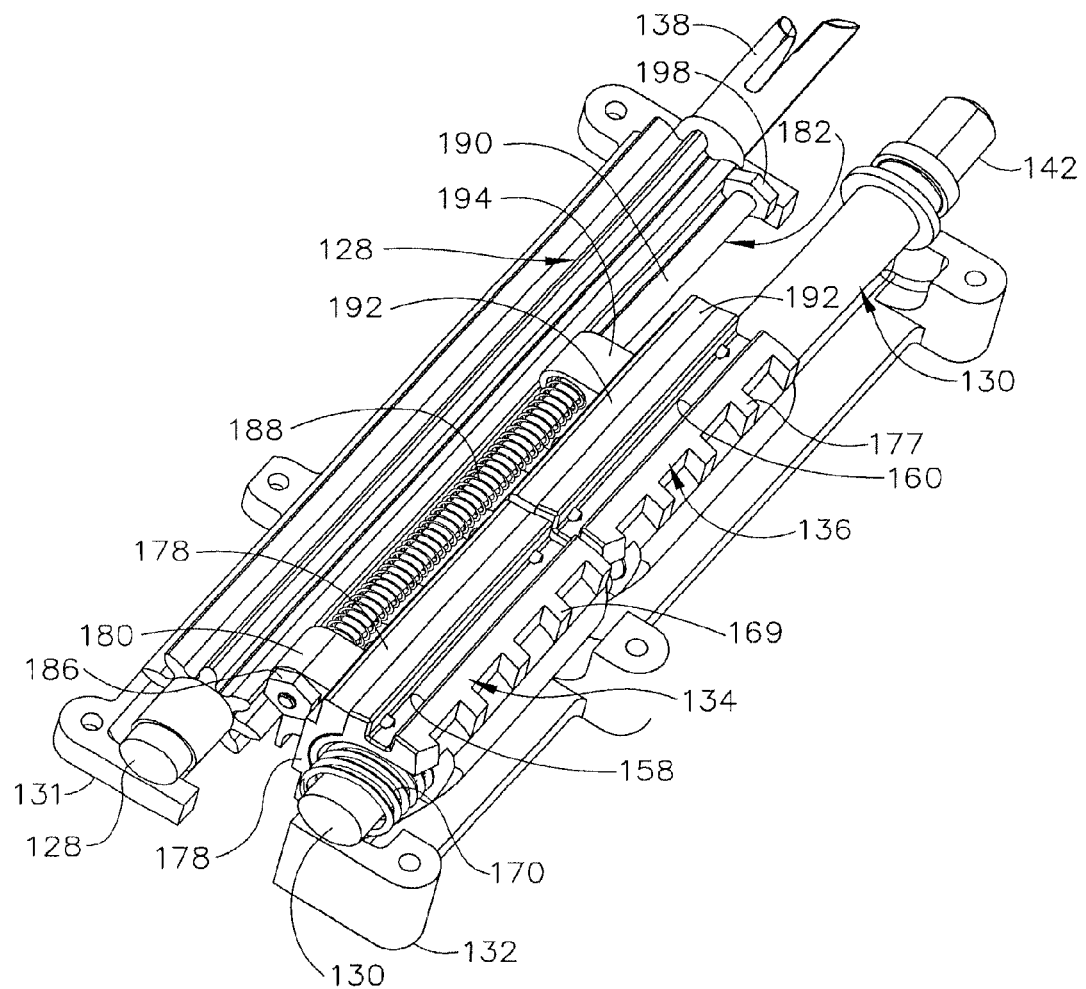
FIG. 8 is a top, left and front isometric view of the carriage frame assembly of FIG. 4 with the upper frame removed.
Figure 9:
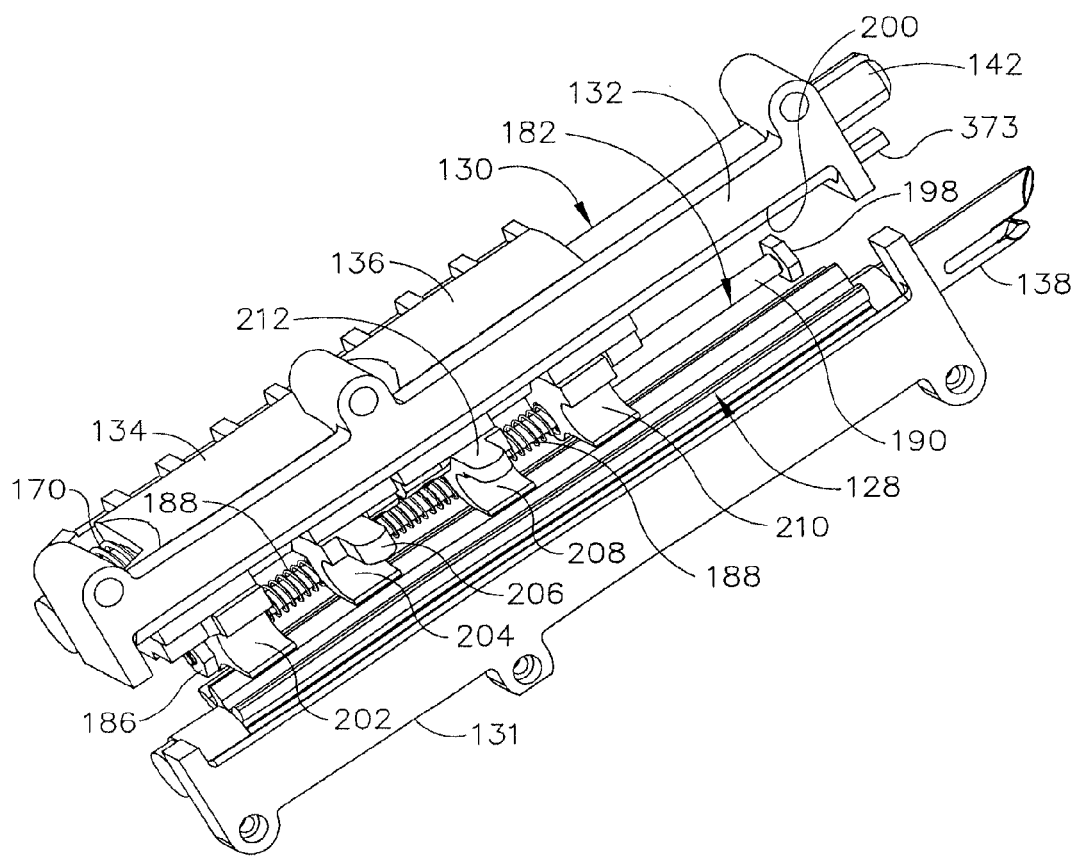
FIG. 9 is a bottom isometric view of the carriage frame assembly of FIG. 8 with the upper frame removed.
Figure 10:
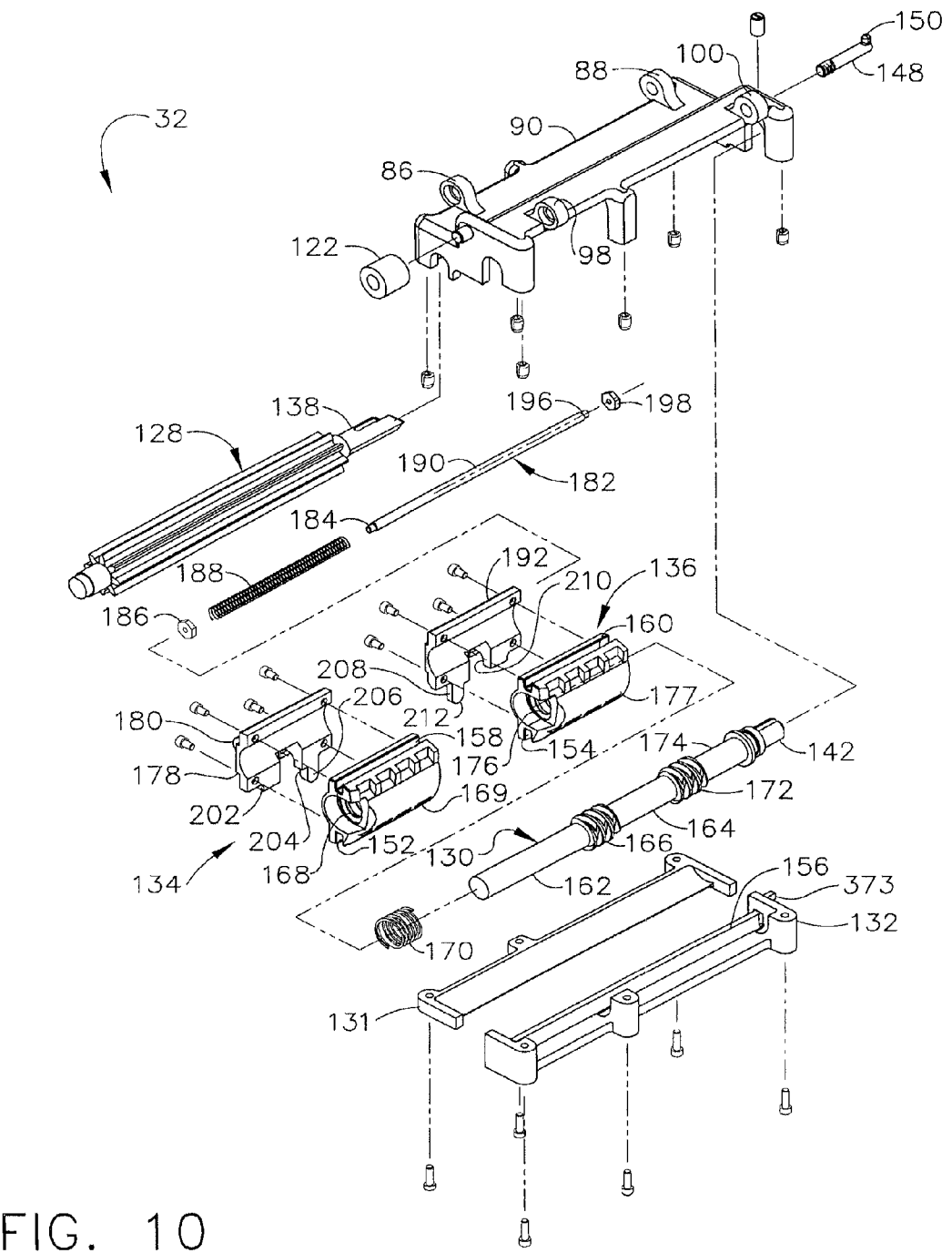
FIG. 10 is a top, left and front isometric exploded view of the carriage frame assembly of FIG. 4.

In FIGS. 7-10, the carriage frame assembly 32 sequences translation of the front and aft carriages 134, 136. With particular reference to FIG. 10, the front and aft carriages 134, 136 respectively include lower longitudinal grooves 152, 154 that slide upon a lower rail 156 upwardly presented on the left lower frame 132. The front and aft carriages 134, 136 respectively include an upper longitudinal groove 158, 160 that slides upon a rail (not shown) downwardly presented on the upper frame 90. The translation shaft 130 has a distal overrun portion 162 and a center overrun portion 164 separated by a front threaded portion 166 that a threaded bore 168 of a front main body portion 169 of the front carriage 134 traverses in response to rotation of the translation shaft 130. A front translation compression spring 170 on the translation shaft 130 distal to the front carriage 134 compresses to allow the front carriage 134 to free wheel when being distally advanced and then biases the front carriage 134 aft to engage the front threaded portion 166 for being retracted upon reversal of rotation of the translation shaft 130.

With particular reference to FIGS. 8 and 10, proximal to the center overrun portion 164 is an aft threaded portion 172 and then a proximal overrun portion 174 that a threaded bore 176 of a back main body portion 177 of the aft carriage 136 traverses in response to rotation of the translation shaft 130 as well as in response to a connection to the front carriage 134. In particular, a front bracket 178 mounted on a right side of the front carriage 134 has a rightward front pin guide 180 that receives a distal end of a longitudinally aligned carriage limiting rod 182. A distal threaded end 184 of the carriage limiting rod 182 extends distally out of the rightward front pin guide 180 and is prevented from backing out by a front nut 186. A long compression spring 188 is received over a shaft 190 of the carriage limiting rod 182 proximal to the rightward front pin guide 180. An aft bracket 192 is attached to a right side of the back main body portion 177 of the aft carriage 136 to extend a rightward aft pin guide 194 that receives the carriage limiting rod 182, which extends a proximal threaded end 196 proximally out of the rightward aft pin guide 194 to receive an aft nut 198 that limits forward movement. The long compression spring 188 biases the aft carriage 136 away from the front carriage 134, delaying retraction of a tissue sample until cutting is complete when full distal translation of the front carriage 134 pulls the aft carriage 136 onto the aft threaded portion 172.

With particular reference to FIG. 9, a lengthwise engagement aperture 200, defined between the right and left lower frames 131, 132, presents engaging structures that actuate the disposable probe assembly 14 and the revolver drum assembly 18. The rotation (spur) gear 128 exposes its left side to the lengthwise engagement aperture 200 for engagement with the rotation spur gear section 68 of the cutter gear 62 to impart a rotation. The front bracket 178 has a downward distal half cylinder recess 202 sized to grip the distal reduced diameter bearing surface 64 of the cutter gear 62 (FIG. 2). The front bracket 178 further has a downward proximal half cylinder recess 204 proximally spaced and sized to grip the proximal reduced diameter bearing surface 66 of the cutter gear 62 (FIG. 2) as well as a downwardly projecting front actuation finger 206 to the left side and below of the cutter gear 62 for effecting atmospheric pressure to the probe cannula 22. Similarly, the aft bracket 192 has a downward distal half cylinder recess 208 and a downward proximal half cylinder recess 210 proximally spaced and sized to nonobstructively translate overtop of a tissue retraction tube 211, as well as a downwardly projecting aft actuation finger 212 that selects vacuum pressure for communicating to the probe cannula 22.

Figure 11:
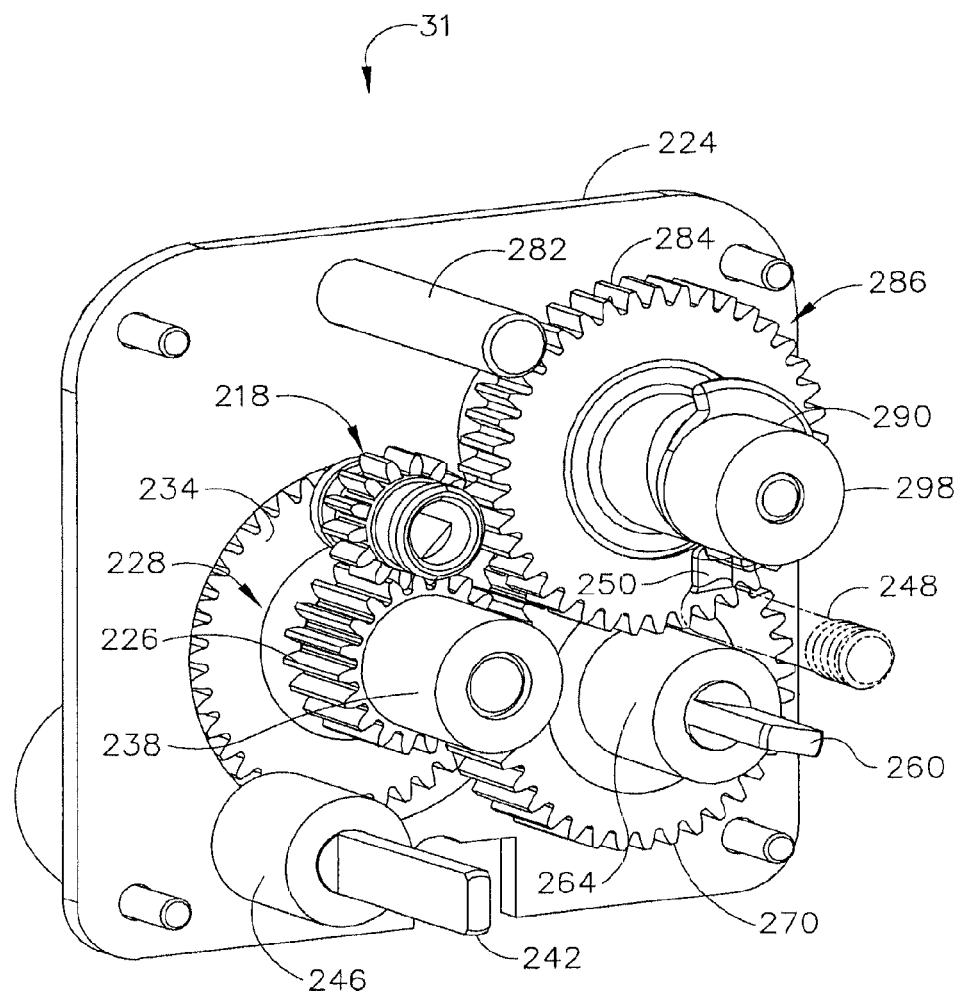
FIG. 11 is a right front view of a transmission section of the motor drive assembly of FIG. 4 with a distal bulkhead removed.
Figure 12:
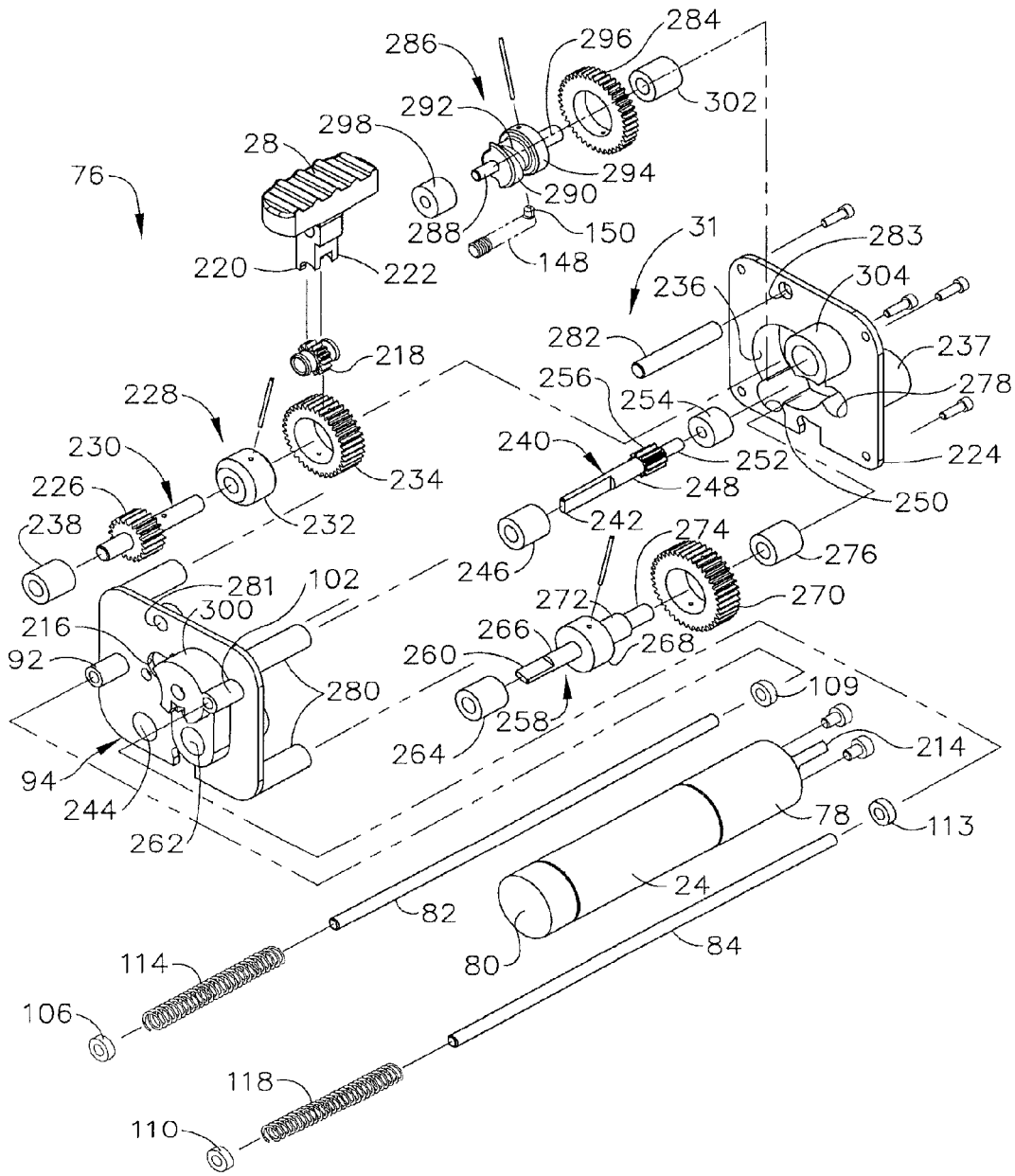
FIG. 12 is a front left exploded view of the transmission section of the motor drive assembly of FIG. 4.

In FIGS. 2-3 and 11-12, the motor drive assembly 76 rotates rotation and translation shafts 128, 130 at a fixed ratio to optimize cutting performance of the cutter tube 36 when the slide button 28 is back. Alternatively, the motor drive assembly 76 imparts a jackhammer vibration to the carriage frame assembly 32 when the slide button 28 is forward. With particular reference to FIGS. 11-12, the planetary gearbox 78 extends proximally a keyed motor drive shaft 214 (FIG. 12) through a drive shaft hole 216 formed in the distal bulkhead 94. A slide spur gear 218 is received upon the keyed motor drive shaft 214 remaining engaged for rotation between a first distal (jack hammer) position and a second proximal (translation) position in accordance with a position of the slide button 28 whose distal and proximal feet 220, 222 straddle the slide spur gear 218. In FIG. 11, the slide spur gear 218 is close to a proximal bulkhead 224 of the transmission section 31, engaging a small spur 226 of a multiplier gear assembly 228. The multiplier gear assembly 228 includes a longitudinal shaft 230 centrally attached to the small spur gear 226. Proximal thereto, a cylindrical hub 232 is pinned to the longitudinal shaft 230 and in turn is encompassed by and pinned to a large spur gear 234 that rotates within a correspondingly sized, distally open recess 236 formed in proximally projecting container 237 integral to the proximal bulkhead 224. A front cylinder bearing 238 received on a distal portion of the longitudinal shaft 230 is received by the proximal surface of the distal bulkhead 94.

A first output drive shaft 240 distally presents a right angle prismatic end 242 shaped to engage the beveled and slotted end 138 of the rotation shaft 128 that passes through a lower right hole 244 in the distal bulkhead 94. A cylindrical spacer 246 is received over a distal cylindrical portion 248 of the first output shaft 240, taking up the space between the rotation shaft 128 and the proximal bulkhead 224. A distally open recess 250, formed as part of the container 237 that communicates from below with the recess 236, is shaped to receive a proximal cylindrical end 252 of the first output drive shaft 240 and encompasses cylindrical bearing 254 as well as a small spur gear segment 256, which is distal thereto and engages the large spur gear 234 of the multiplier gear assembly 228.

A second output drive shaft 258 distally presents a right angle prismatic end 260 to engage the proximal slotted end 142 of the translation shaft 130 that extends through a low left hole 262 in the distal bulkhead 94. A cylindrical spacer 264 is received over a distal cylindrical portion 266 of the second output drive shaft 258 proximal to the right angle prismatic end 260 and distal to a wider diameter hub segment 268 that is encompassed by and pinned to a large spur gear 270 that engages the small spur gear 226 of the multiplier gear assembly 228. Proximal to the hub segment 268 is a wide spacer segment 272 and then a narrow cylindrical end 274 that receives a cylindrical bearing 276 that resides within a correspondingly-sized, distally open recess 278 that communicates from the left with the recess 236 and is formed as part of the same container 237.

The distal and proximal bulkheads 94, 224 are structurally attached to one another in parallel alignment traverse to the longitudinal axis of the biopsy device 10 by cylindrical legs 280 molded to and proximally projecting from rectangular corners of the distal bulkhead 94 and fastened to the proximal bulkhead 224. In addition, a pin 282 passes through holes 281, 283 longitudinally aligned in the distal and proximal bulkheads 94, 224 respectively along a top surface.

When the slide button 28 is moved distally to the jackhammer position, the sliding spur gear 218 disengages from the small spur gear 226 and engages a large spur gear 284 of a rotary camming gear assembly 286. A camming shaft 286 from distal to proximal includes a distal cylindrical end 288, a cam wheel 290, a mid-shaft portion 292 that receives the upwardly directed strike pin 150 of the proximally projecting bolt 148, a wide diameter hub 294 that is encompassed by and pinned to the large spur gear 284, and a proximal cylindrical end 296. A distal cylindrical bearing 298 is received within a proximally open container 300 projecting distally from the distal bulkhead 94 and in turn receives the distal cylindrical end 288 of the camming shaft 286. A proximal cylindrical bearing 302 is received within a distally projecting and open cylinder 304 formed on the proximal bulkhead 224 and in turn receives the proximal cylindrical end 296 of the camming shaft 286.

As the camming shaft 286 rotates clockwise as viewed from behind, the cam wheel 290 presents a proximal surface to the distal edge of the strike pin 150 that is more proximal until the interrupted portion of the camming wheel 290 is presented, allowing the strike pin 150 to return to a distal position under the urging of the distal biasing of the right and left compression springs 114, 118.

Figure 13:
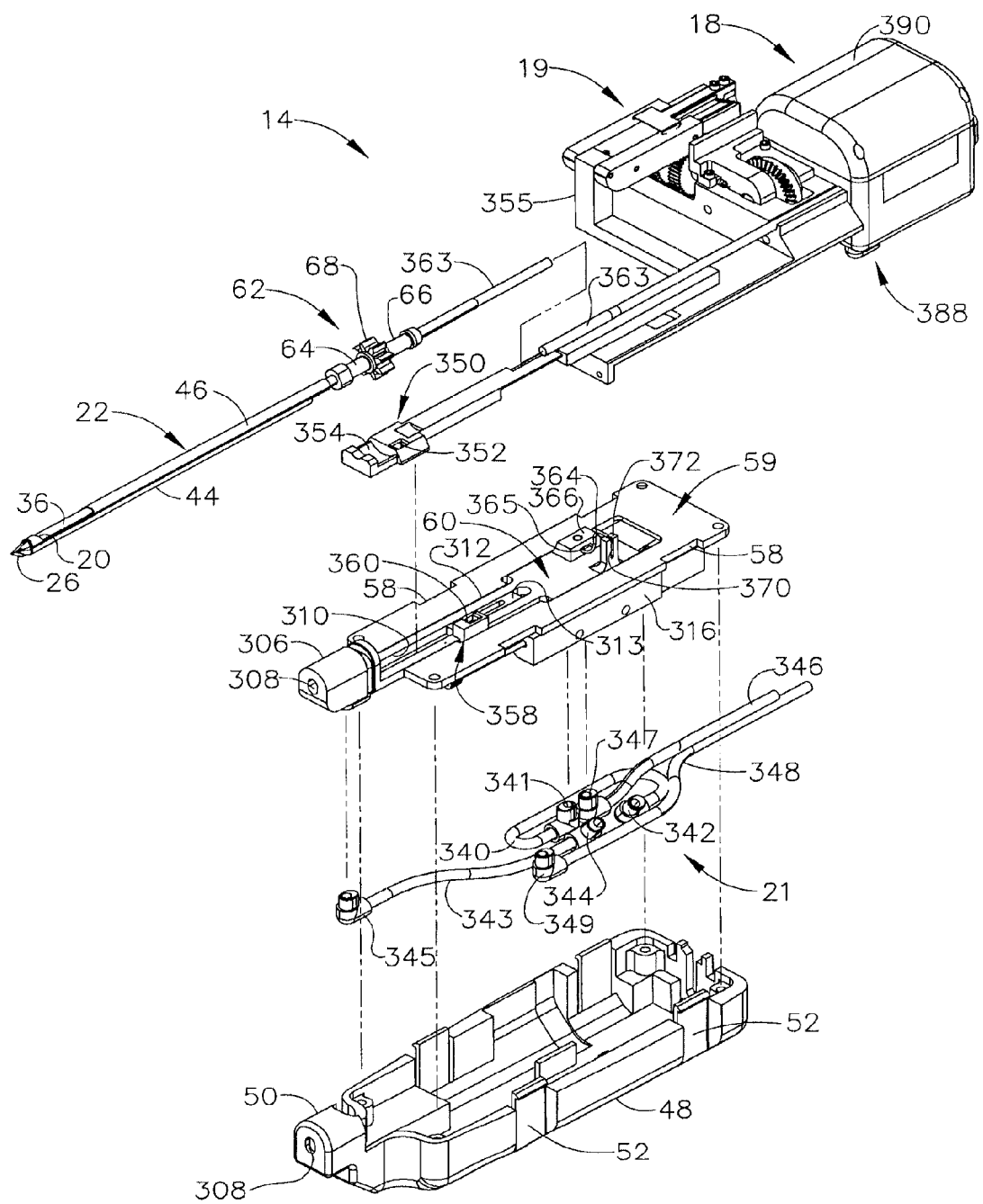
FIG. 13 is a left front isometric view of the disposable probe assembly of FIG. 1 with a hand-held distal portion partially disassembled from the sample revolver drum assembly.
Figure 14:
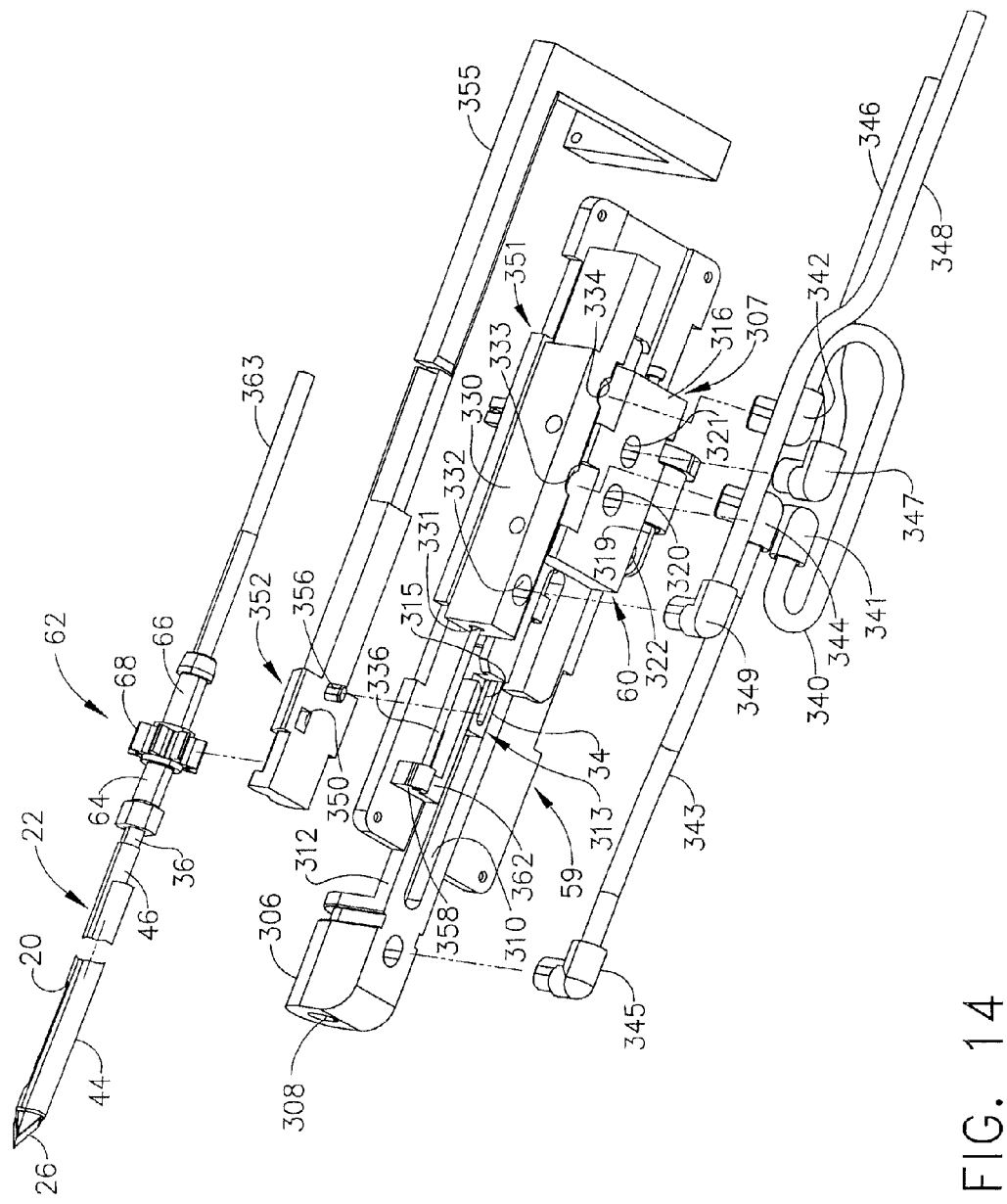
FIG. 14 is an isometric view from below and to the left of the hand-held distal portion of the disposable probe assembly of FIG. 13 with cover components omitted.
Figure 15:
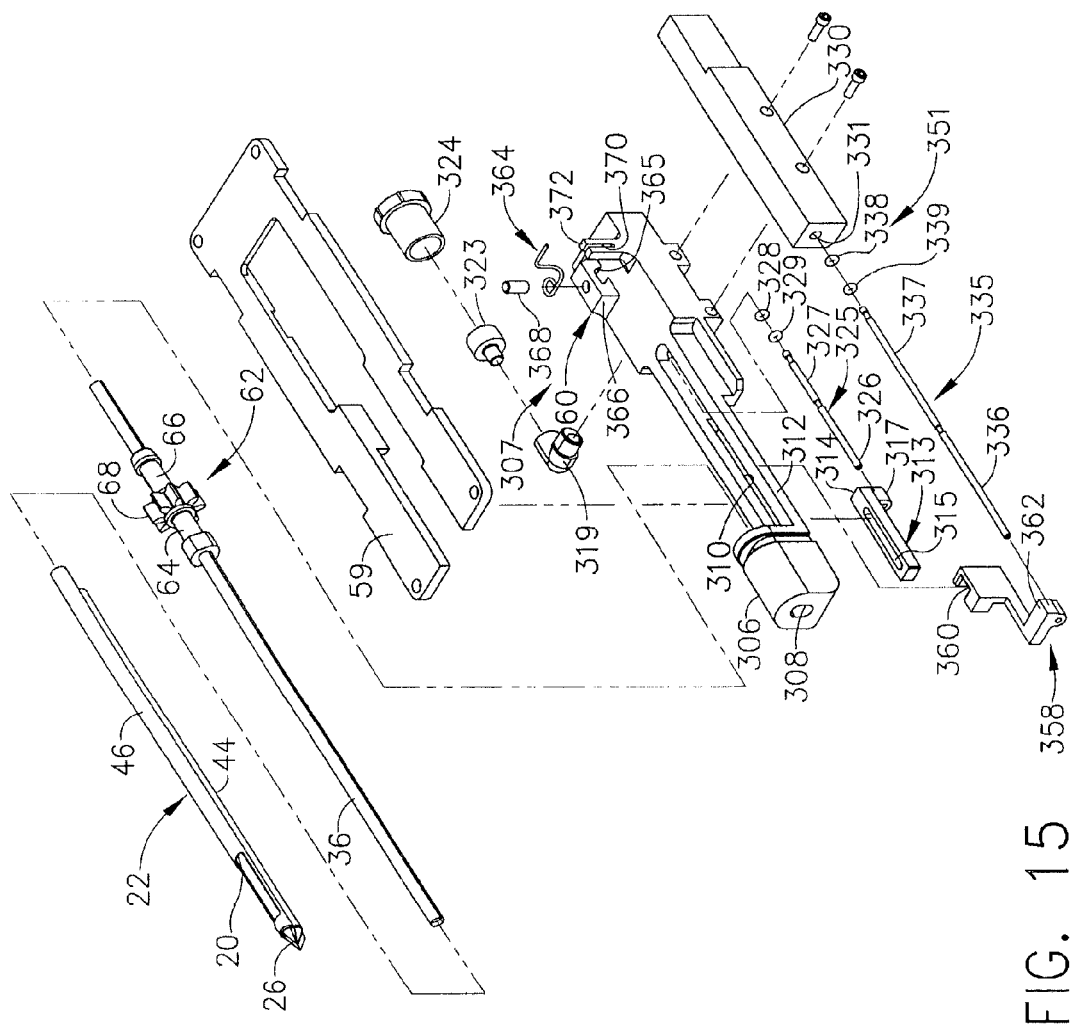
FIG. 15 is an isometric view of an exploded portion of the disposable probe assembly.

DISPOSABLE PROBE ASSEMBLY. In FIGS. 13-29, the disposable probe assembly 14 has movable components that respond to the actuating motions of the reusable handpiece 12. With particular reference to FIGS. 13-15, the distal portion 21 of the disposable probe assembly includes the probe cannula 22 that is supported by the probe support body 60. The probe support body 60 includes a distal probe mount 306 that is received within the distal probe mount cover 50 of the bottom cover 48. The front carriage 134 controls a vacuum valve 307. In particular, proximal to and underlying a longitudinal axis of the disposable probe assembly 14 defined by a probe guide hole 308 passing through the distal probe mount 306, a vertically open longitudinal trough 310 is formed into a necked portion 312 of the probe support body 60. A cutter carriage-driven vacuum valve driver 313 has an elongate driver body 314 that longitudinally translates within the longitudinal trough 310 and upwardly presents an elongate slot 315 for being indirectly moved by the downwardly projecting front actuation finger 206 of the front carriage 136.

Figure 23:
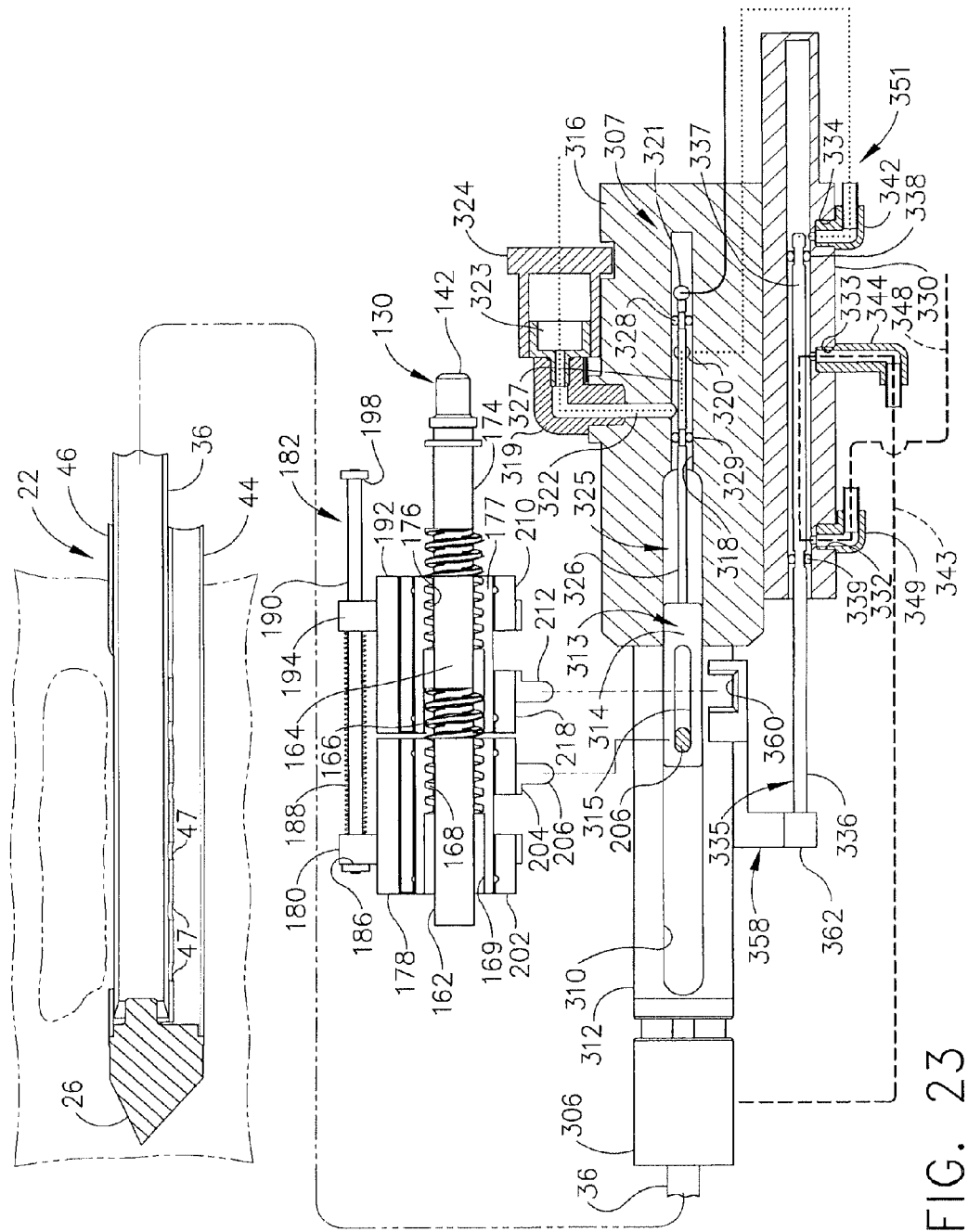
FIG. 23 is a diagrammatic view of the hand-held distal portion of the disposable probe assembly of FIG. 1 with both carriages advanced for closing a side aperture in a probe cannula for insertion into tissue.

With reference also to FIG. 23, a proximal block portion 316 is attached to the necked portion 312 of the probe support body 60. A lower mounting 317 extends from the elongate driver body 314 distal to and longitudinally aligned with a distally open, longitudinally aligned vacuum valve bore 318 (FIG. 23) formed in proximal block portion 316 of the probe support body 60. Central and proximal ports 320, 321 communicate with the vacuum valve bore 318 from an underside of the proximal block portion 316 and a distal port 322 communicates laterally from a right side of the proximal block portion 316. A right distal 90-degree fitting 319 communicates between the distal port 322 and an intake filter 323 within an outer hose fitting 324.

A vacuum valve control rod 325 has a distal actuating portion 326 extending distally out of the valve bore 318 with a distal end positionable under the downwardly open portion of the longitudinal trough 310 and attached to the lower mounting 317 of the vacuum valve driver 313. The vacuum valve control rod 325 also has a valve spool portion 327 that longitudinally translates within the valve bore 318 to selectively position between a first position and a second position. A proximal O-ring 328 near a proximal end of the valve spool portion 327 and a distal O-ring 329 are spaced such that the first position entails the O-rings 328, 329 bracketing the central and distal ports 320, 322 and the second position entails the O-rings 328, 329 bracketing the proximal and central ports 321, 320, respectively.

The aft carriage 136 controls an air valve 351. In particular, an air valve body 330 is attached to a left side of the proximal block portion 316 and includes a distally open longitudinal air valve bore 331 (FIG. 23) depicted in FIG. 14 as accessed by a distal left port 332, a left center port 333, and a left proximal port 334. An air valve control rod 335 has a distal actuating portion 336 extending distally out of the air valve bore 331. The valve control rod 335 also has a valve spool portion 337 that longitudinally translates within the air valve bore 331 to selectively position between a first position and a second position. A proximal O-ring 338 near a proximal end of the valve spool portion 337 and a distal O-ring 339 are spaced such that the first position entails the O-rings 338, 339 bracketing the central and distal ports 333, 332 and the second position entails the O-rings 338, 339 bracketing the proximal and central ports 334, 333, respectively.

A valve connecting vacuum conduit 340 has one end attached to a lower center ninety-degree fitting 341 attached to the central port 320 of the vacuum valve bore 318 and the other end attached to an aft left ninety-degree fitting 342 that communicates with the left proximal port 334 of the air valve bore 331. A distal conduit 343 is attached at one end to a center ninety-degree fitting 344 that communicates with the left center port 333 and at the other end at a probe union ninety-degree fitting 345 that communicates with the lateral lumen 44. A vacuum supply conduit 346 is attached at one end to a distal ninety-degree fitting 347 that communicates with the proximal port 321 and at the other end to a vacuum supply (not shown). An air supply conduit 348 is attached at one end to a distal ninety-degree fitting 349 that communicates with the distal left port 332 and the other end to an air supply (not shown).

The front actuation finger 206 of the front carriage 136 (FIGS. 9-10) is received within an upwardly open socket 350 formed on a left side of a cutter carriage-driven indexing shuttle 352 having a lateral concave recessed band 354 shaped to encompass with a clearance a lower portion of the rotation spur gear section 68 of the cutter gear 62. An indexing arm 355 attached to the indexing shuttle 352 includes a proximally directed portion that proximally terminates in a rightward portion that terminates in an upward portion. In FIG. 14, a downwardly projecting vacuum actuator lug 356 (FIG. 14) attached to an underside of the indexing shuttle 352 is received within the elongate slot 315 of the vacuum valve driver 314 to selectively communicate the vacuum supply to the probe cannula 22. An air shuttle 358 longitudinally rides on a left edge of the necked portion 312 of the probe support body 60 and upwardly projects an air valve tab socket 360 positioned to receive the aft actuating finger 212 of the aft carriage 138. A downward mounting arm 362 of the air shuttle 358 is attached to the distal actuating portion 336 of the air valve control rod 335 extending distally out of the air valve bore 331.

A straw hook wire 364 supports a midpoint of a sample retraction tube 363 in place upon the probe support body 60 prior to engagement with the reusable handpiece 12. A curled lower right end passes into leftwardly opening 365 along the top right surface of the proximal block portion 316 of the probe support body 60 into a small mounting block 366 extending upwardly from a right side with a downwardly inserted pin 368 passing through the curled lower right end to hold the straw hook wire 364 in place. The straw hook wire 364 has a horizontal portion attached to the curled end that passes under the sample retraction tube 363, bending upward and then bending leftward and horizontally again through a lateral slot 370 in a vertical wire support member 372 formed onto a left side of the top surface of the proximal block portion 316. It should be appreciated that engagement of the reusable handpiece 12 forces the left portions of the straw hook wire 364 out of engagement with the midpoint indented feature 350 as a rib feature 373 (FIG. 9) deflects the left portion of the straw hook wire 364. This facilitates commonality with disposable probe assemblies in which the straw hook wire 364 keeps a translating sample retraction straw in place prior to mounting to the reusable handpiece 12 (not shown).

Figure 16:
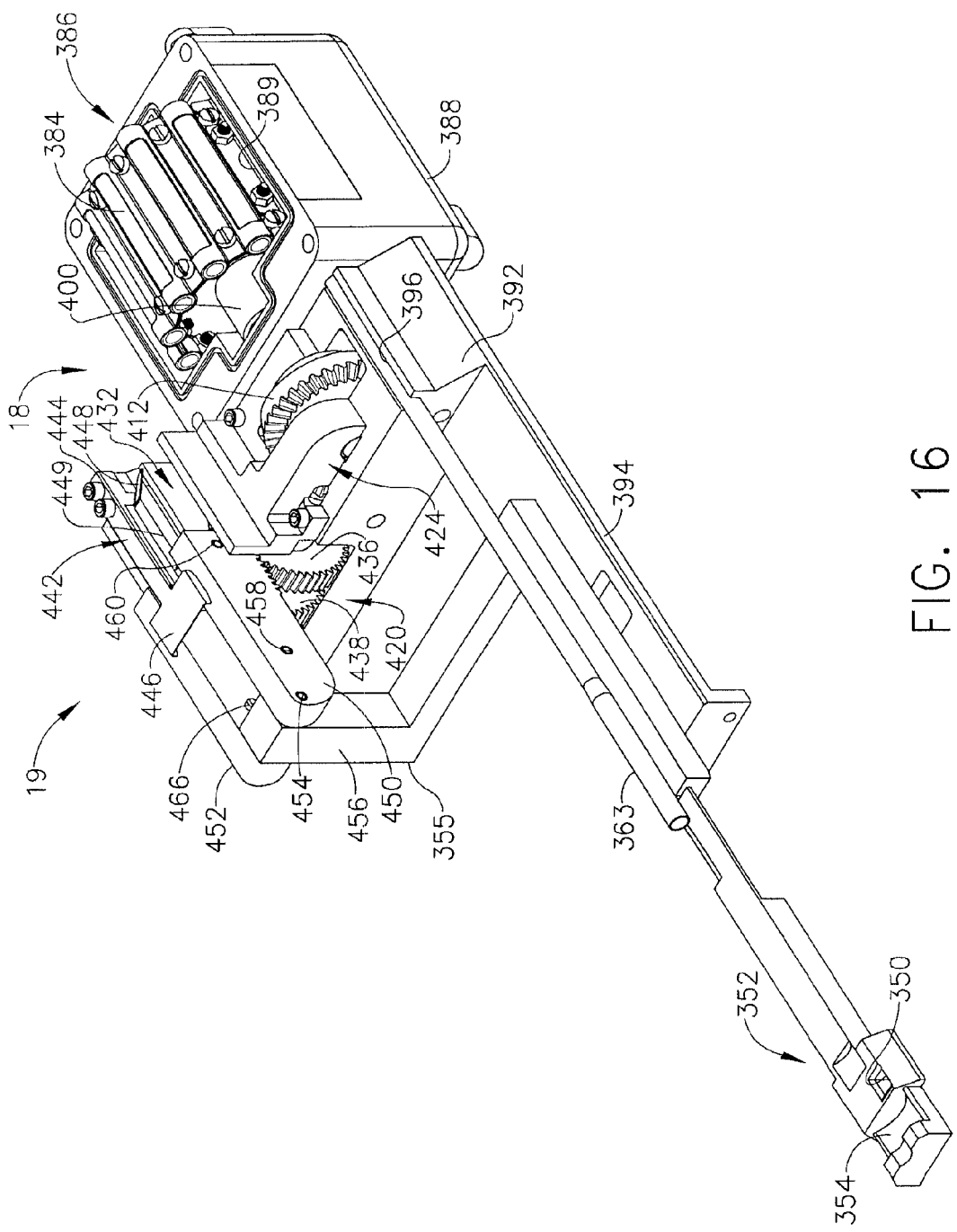
FIG. 16 is an isometric view of the sample revolver drum assembly of FIG. 1.
Figure 17:
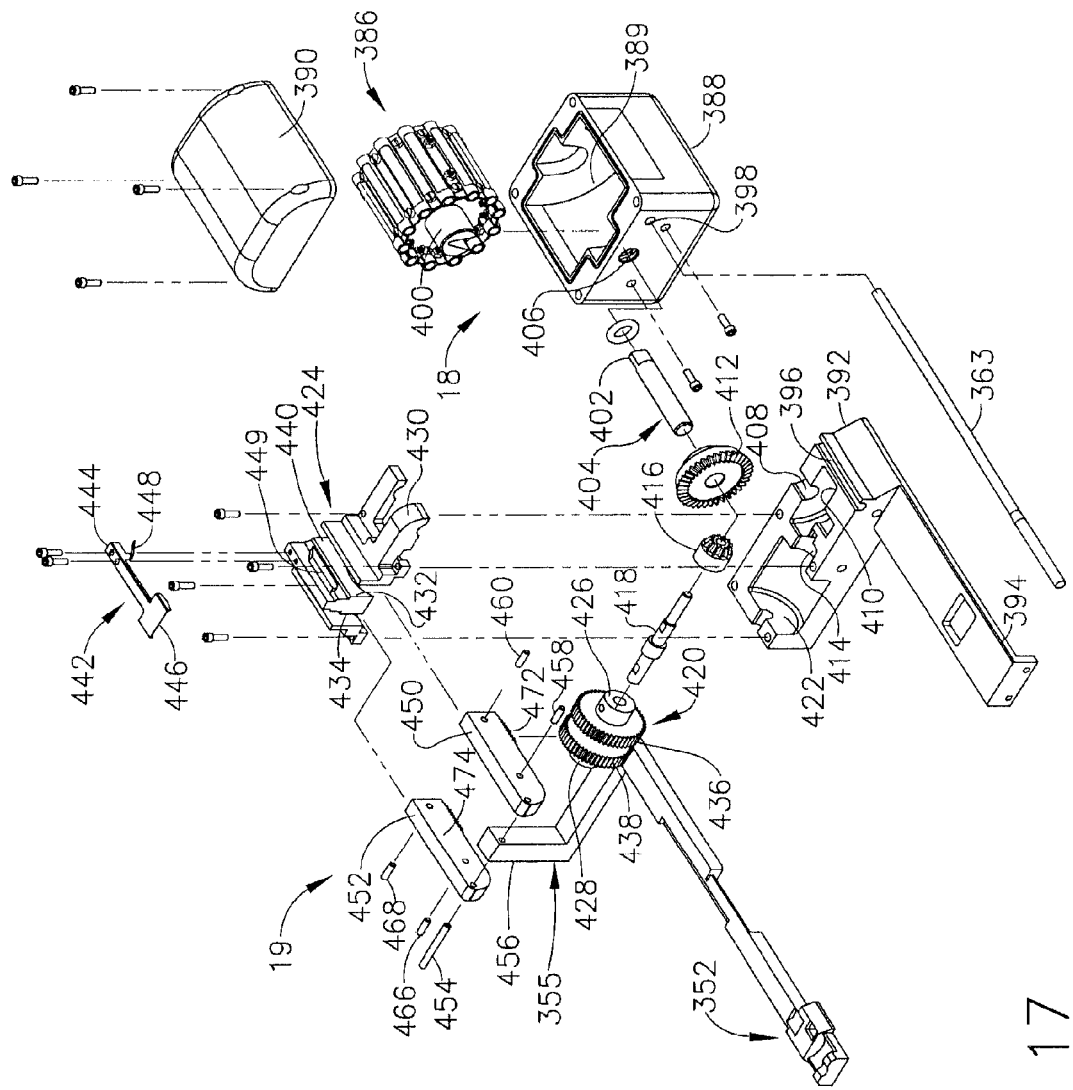
FIG. 17 is an exploded view of the sample revolver drum assembly of FIG. 16.
Figure 20:
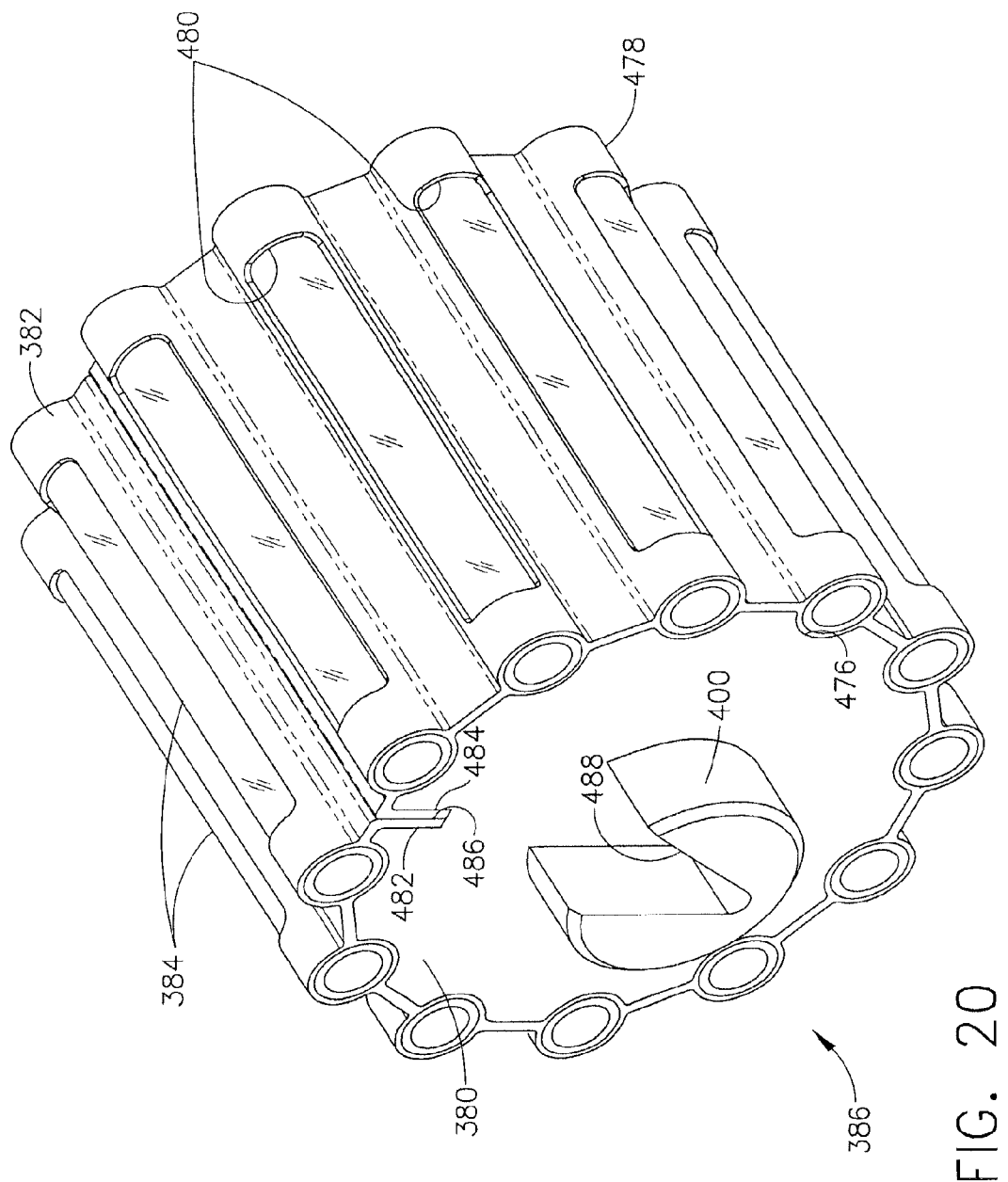
FIG. 20 is an isometric view of a revolver cylindrical drum assembly of the sample revolver drum assembly of FIG. 16.

With particular reference to FIGS. 16-17, the sample revolver drum assembly 18 includes a revolver cylindrical drum 380 encompassed by a detachable revolver drum belt 382 that in turn holds removable sample vials 384 forming a revolver cylindrical drum assembly 386 (FIG. 20). A drum base 388 includes a half cylinder recess 389 which holds the sample revolver drum assembly 386 for rotation about the longitudinal axis and is closed by a top drum cover 390, which may be transparent for monitoring progress in tissue collection or opaque. An indexer support base 392 of the indexing assembly 19 has a proximal surface fastened to a distal surface of the drum base 388 and extends a mounting flange 394 distally to attach to a proximal end of the hand-held distal portion 21 of the disposable probe assembly 14. The sample retraction tube 363 passes over the mounting flange 394 and is gripped within a longitudinal groove 396 formed along a top, left side of the indexer support base 392 and passes through a hole 398 on a top left corner of a distal face of the drum base 388.

A slotted distal drum axle 400 of the revolver cylindrical drum 380 is received within a smaller distal portion of the half cylinder recess 389 and a proximal drum axle 401 (FIG. 21) is received within a smaller proximal portion of the half cylinder recess 389. The slotted distal drum axle 400 receives an angled proximal end 402 of a shaft 404 that passes through a shaft hole 406 in the drum base 388. A distal portion of the shaft 404 is received within a shaft recess 408 across the top of the indexer support base 392 that communicates with a half cylindrical gear recess 410 that encompasses a lower half of a large bevel gear 412 mounted on the shaft 404. A small half cylindrical gear recess 414 receives a transversely oriented small bevel gear 416 that engages the large bevel gear 412. A transverse shaft 418 has a left end mounted to the small bevel gear 416 and a right end mounted to a dual spur gear assembly 420 that rotates within a rightward transverse half cylindrical recess 422 formed in the indexer support base 392.

Figure 18:
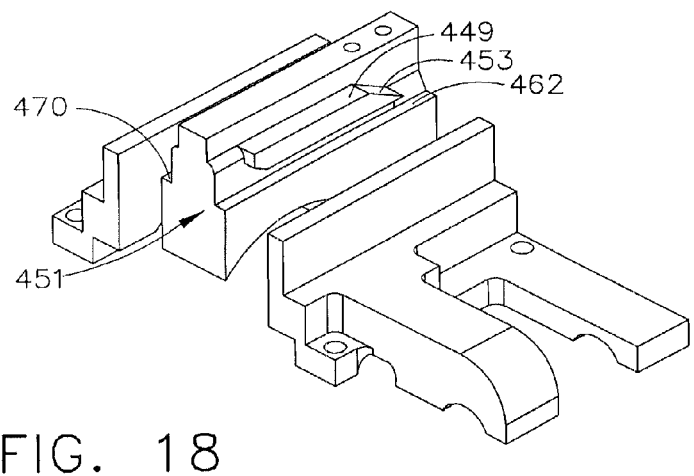
FIG. 18 is an isometric detail view of an indexer gear cover of the sample revolver drum assembly of FIG. 16.

With particular reference to FIG. 18, a top indexer gear cover 424 mounts overtop of the indexer support base 392 that contacts the top surfaces of the shaft 404 and left and right axle ends 426, 428 of the dual spur gear assembly 420 with a leftward slot 430 that exposes a top portion of the large bevel gear 412 and distally open left and right vertical slots 432, 434 that expose top surfaces of a left and right spur gear 436, 438 of the dual spur gear assembly 420. In FIG. 17-18, a central beam 440, defined between the left and right vertical slots 432, 434, has a T-shaped hold down spring 442 mounted on top with its narrow end 444 mounted to a proximal end of the central beam 440. A laterally wider end 446 extends overtop of both vertical slots 432, 434. A cyclic spring gate 448 extends laterally to the left and right from a proximal end of the T-shaped hold down spring 442 and ramps downwardly and proximally.

With particular reference to FIG. 18, each side of the central beam 440 has a respective left and right lower pin guides 462, formed as an upper surface of a wider lower portion. An upper pin guide 449 extends laterally out from the central beam 440 on each side and is spaced respectively above the lower pin guides 462, 470 to form a lower pin channel 451. Although only the left upper pin guide 449 is depicted, it should be appreciated that the right side includes a mirror image upper pin guide. A rear ramped portion 453 of the upper pin guide 449 underlies and supports the cyclic spring gate 448.

Left and right cyclic arms 450, 452 have distal ends mounted on respective ends of a transverse cyclic axle 454 whose central portion passes through a top end 456 of the index arm 355. Left fore and aft cyclic pins 458, 460 extend rightward out of the left cyclic arm 450. Right fore and aft cyclic pins 466, 468 extend leftward out of the right cyclic arm 452. Each cyclic arm 450, 452 includes a respective left and right bottom rack segment 472, 474 close to the distal rotating end positioned to engage a respective spur gear 436, 438 under the downward urging of the laterally wider distal end 446 of the T-shaped hold spring 442.

Figure 19A:
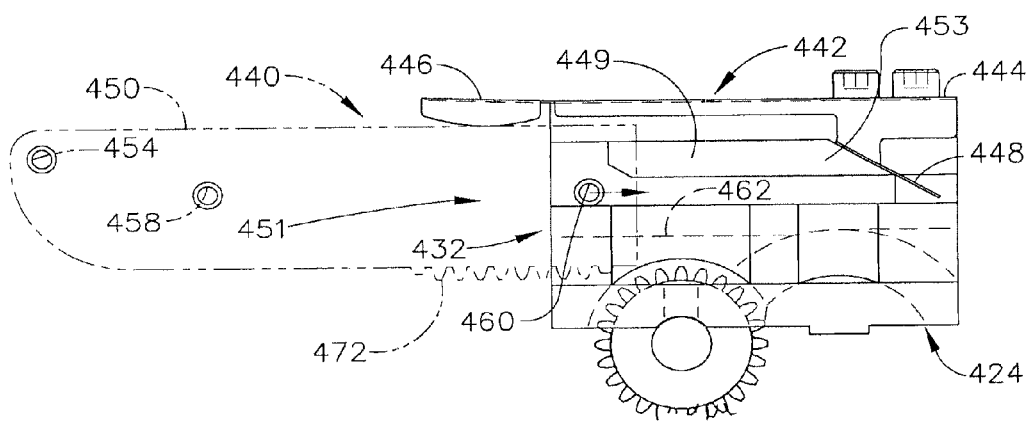
FIG. 19A is a left side diagrammatic view of a left cyclic arm shown in phantom down for engagement during a proximal stroke engaged to the indexer gear cover of FIG. 18.
Figure 19B:
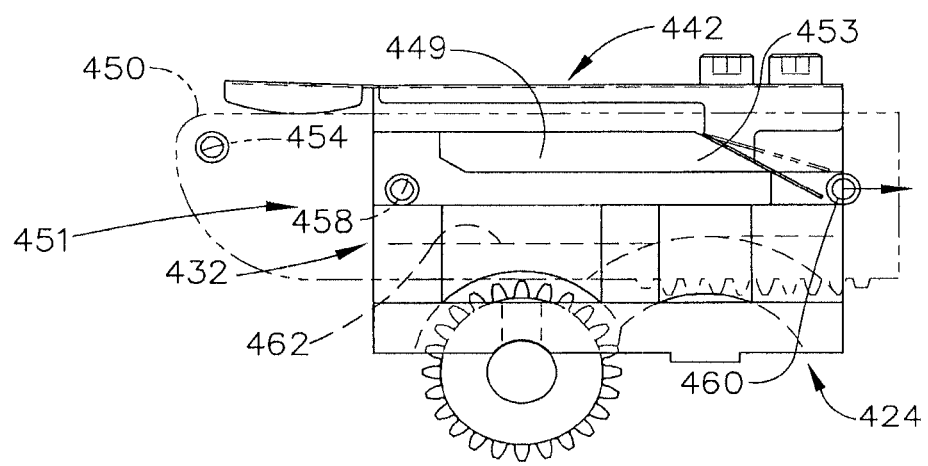
FIG. 19B is a left side diagrammatic view of the left cyclic arm shown in phantom at a proximal most position on the indexer gear cover of FIG. 18.
Figure 19C:
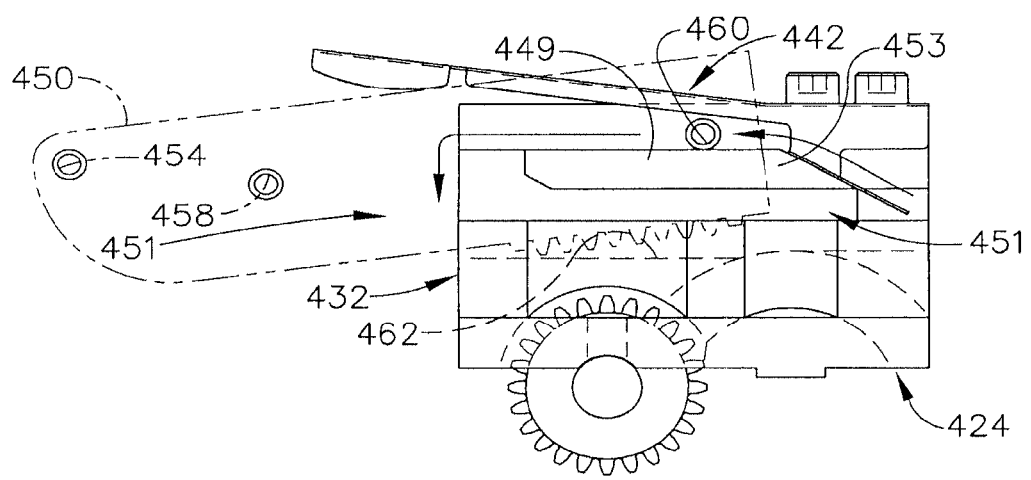
FIG. 19C is a left side diagrammatic view of the left cyclic arm shown in phantom during a return distal stroke rotated upward for disengagement.

With reference to FIG. 16, the left cyclic arm 450 is at its distal most position. It should be appreciated that the left aft cyclic pin 460 is distal to the upper pin guide 449. In FIG. 19A, proximal movement of the right cyclic arm 450 presents the rack segment 472 to rotate the left spur gear 436 (not shown in FIG. 19A) top aft, held in engagement by the T-shaped hold down spring 442. Proximal movement of the cyclic arms 450, 452 causes the dual spur gear assembly 420 and thus the small bevel gear 416 to rotate top aft, which in turn causes the large bevel gear 412 and revolver cylindrical drum assembly 386 to rotate top right, indexing the sample vial 384 to the sample retraction tube 363 in the hole 398. In FIG. 19B, the right cyclic arm 450 has reached its proximal most position, wherein the left aft pin 460 has pushed through the cyclic spring gate 448 and out of the lower pin channel 451. In FIG. 19C, upon distal movement of the right cyclic arm 450, the left aft pin 460 rides up the cyclic spring gate 448, rotating the right cyclic arm 450 out of engagement with the left spur gear 436. It should be appreciated that the left aft pin 460 will drop off of the front of the upper pin guide 449 as the distal most position is reached and be positioned to enter again the lower pin channel 451 under the downward urging the T-shaped hold down spring 442.

Figure 21:
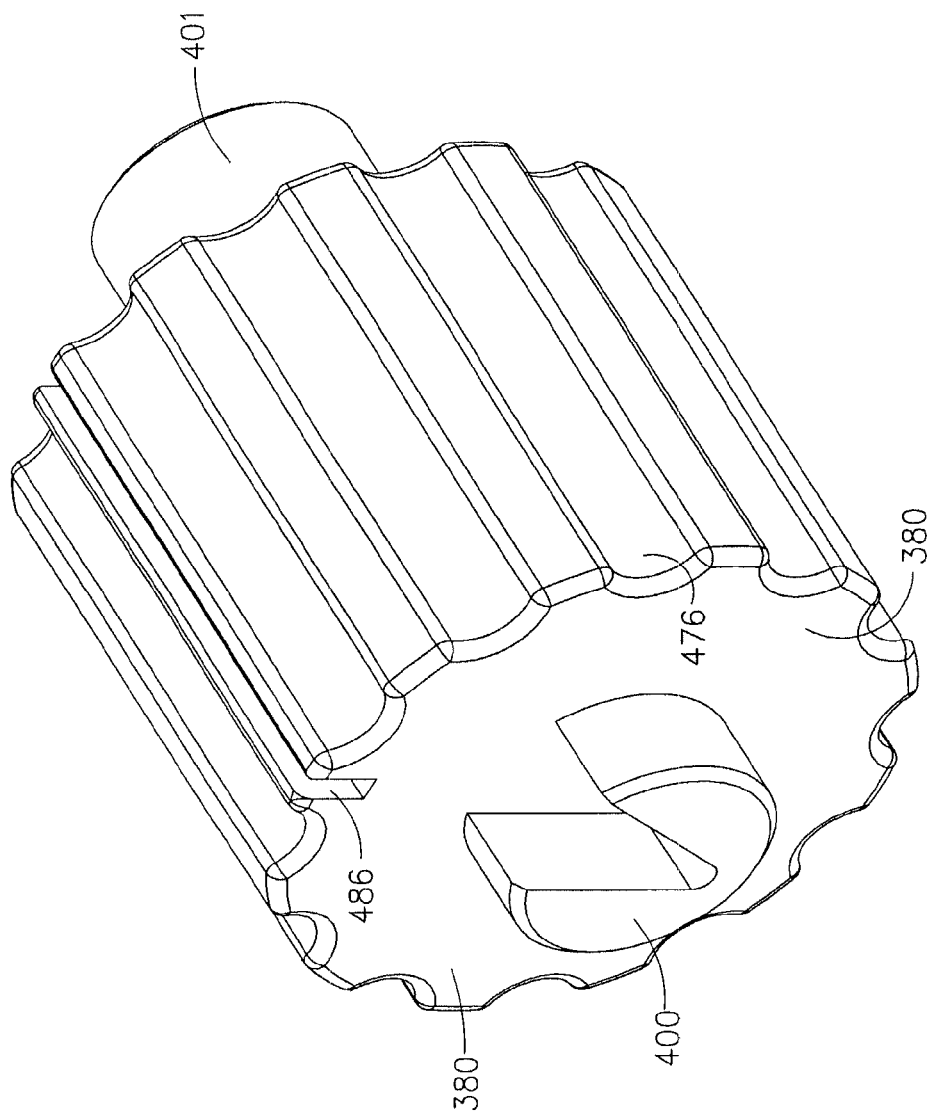
FIG. 21 is an isometric view of the revolver cylindrical drum of the revolver cylindrical drum assembly of FIG. 20.
Figure 22:
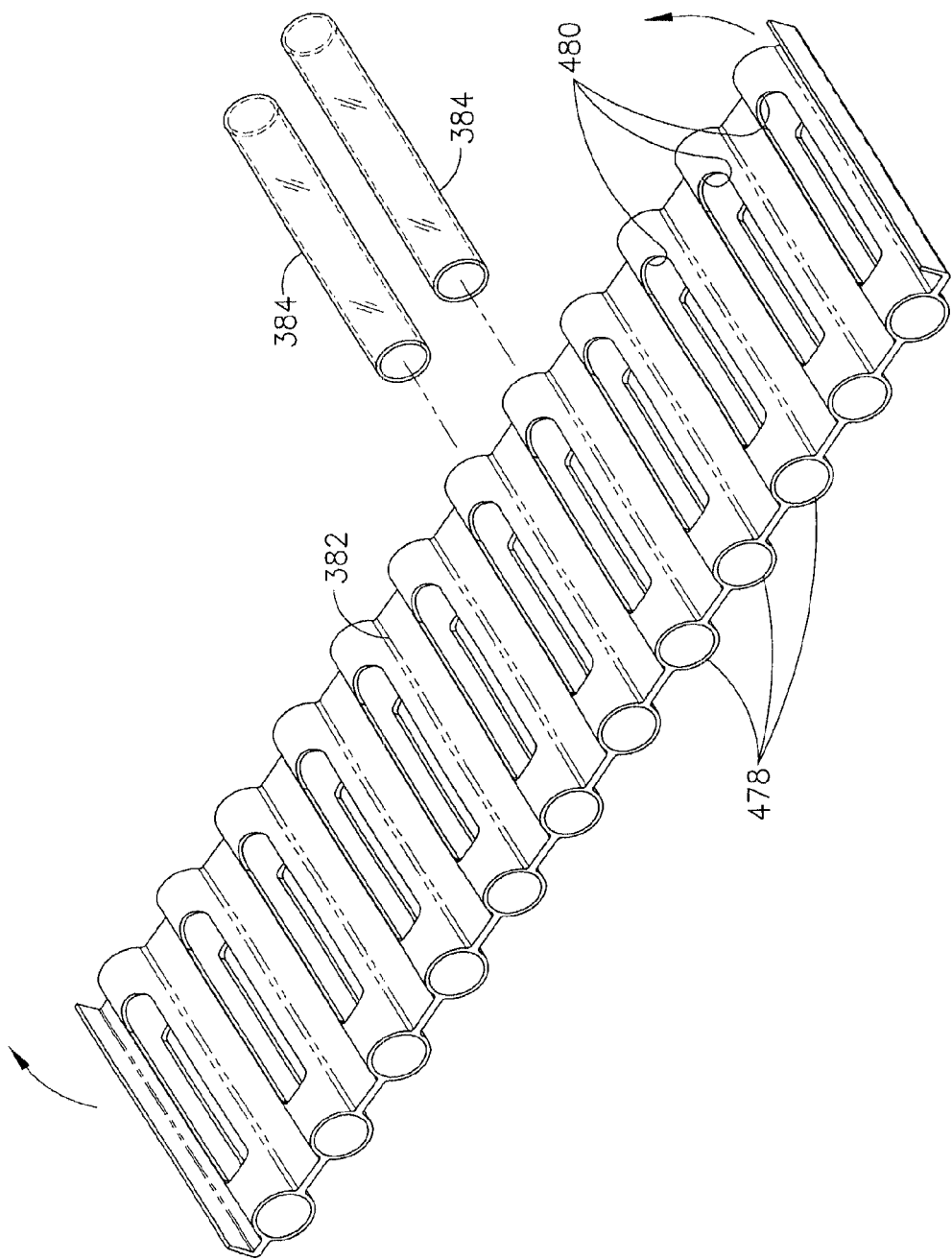
FIG. 22 is an isometric view of a revolver drum belt with a couple of removed sample vials of the revolver cylindrical drum assembly of FIG. 20.

In FIGS. 20-22, the revolver cylindrical drum 380 includes radially spaced longitudinal recesses 476 shaped to receive respective cylindrical vial holders 478 formed in the revolver drum belt 382 that hold the sample vials 384. Each vial holder 478 includes an elongate outward aperture 480 so that contents of the retained vial 384 may be viewed. In order that pathology may ascertain which sample vial 384 received the first and subsequent tissue samples, the revolver drum belt 382 terminates in first and second belt retaining ears 482, 484 that are drawn into longitudinal abutment and inserted into a longitudinal indexing and retention slot 486 formed in the revolver cylindrical drum 380 as the circled revolver drum belt 382 is slid longitudinally onto the revolver cylindrical drum 380. A V-shaped slot 488 of the slotted distal drum axle 400 assures that the angled proximal end 402 of the shaft 404 is in an initial condition with a narrow aspect upward to receive the open side of the V-shaped slot 488, which registers the retaining ears 482, 484 to a known position prior to commencing sampling.

In FIGS. 23-29, the operation of the reusable handpiece 12 and the hand-held distal portion 21 of the disposable probe assembly 14 are depicted sequentially in diagrammatic form to illustrate how the indexing assembly 19 and revolver drum assembly 18 are operated in conjunction with the taking of vacuum assisted core biopsy samples. In FIG. 23, the hand-held distal portion 21 of the disposable probe assembly 14 has both carriages 134, 136 distally advanced in an initial state for closing the side aperture 20 in the probe cannula 22 for insertion into tissue. The front carriage 134 also advances the cutter carriage-driven vacuum valve driver 313 to its distal position, switching the vacuum valve 307 distally to provide atmospheric pressure to the air valve 351 (i.e., atmosphere in distal port 322 and out center port 320 to left proximal port 334). The aft carriage 136 positions the air valve 351 to shut off the input from the vacuum valve 307, instead causing the air supply conduit 348 to communicate through the left distal port 332 to the left center port 333 to the distal conduit 343 to pressurize the lateral lumen 44.

Figure 24:
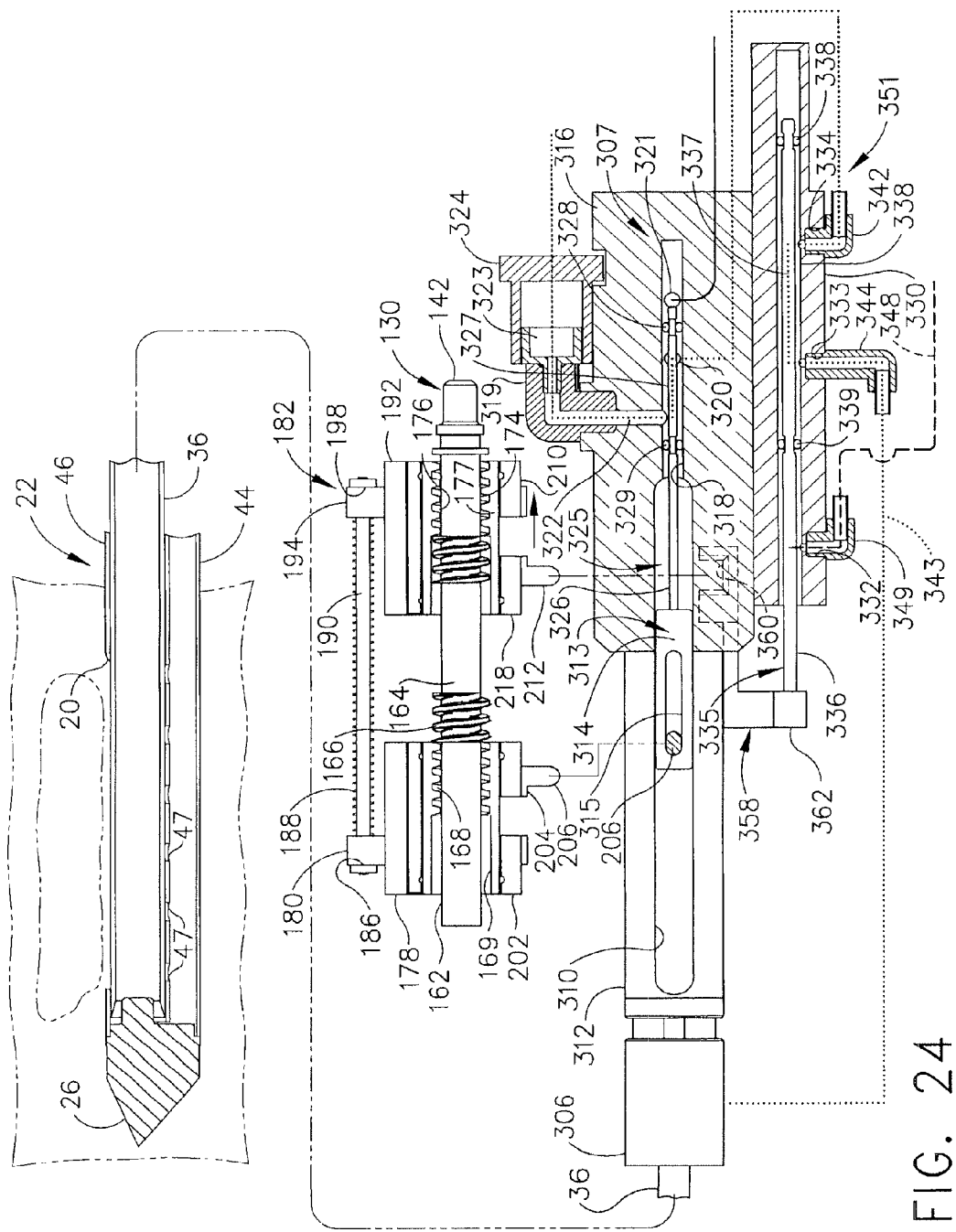
FIG. 24 is a diagrammatic view of the hand-held distal portion of the disposable probe assembly of FIG. 1 with an aft carriage retracted to vent the probe cannula to the atmosphere to begin a new sample taking cycle.

In FIG. 24, the aft carriage 136 has proximally retracted, switching the air valve 351 so that the atmospheric pressure provided by the vacuum valve 307 now communicates through the left proximal port 334 to the left center port 334 to the distal conduit 343 to the lateral lumen 44, venting the probe cannula 22 to begin a new sample taking cycle.

Figure 25:
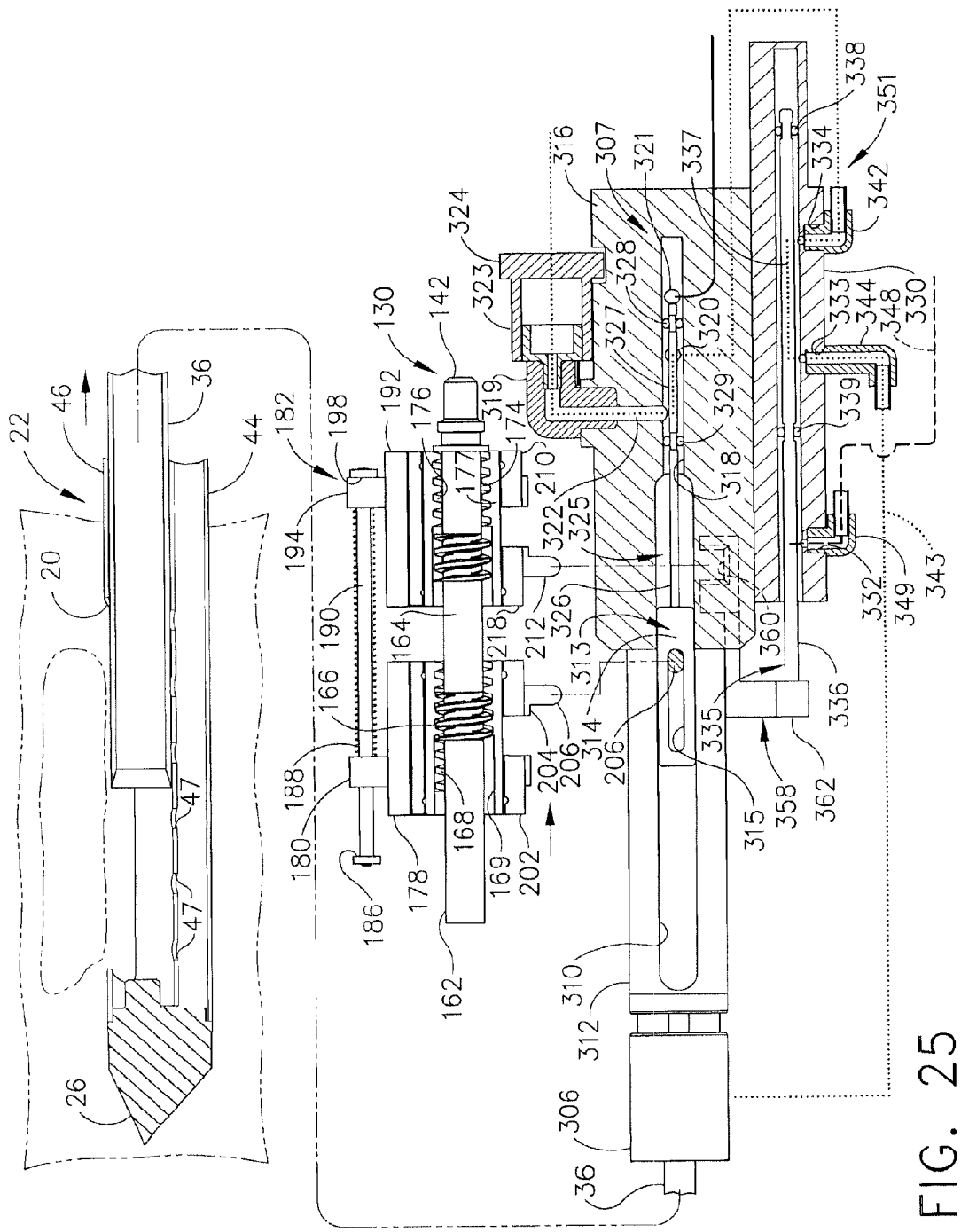
FIG. 25 is a diagrammatic view of the hand-held distal portion of the disposable probe assembly of FIG. 1 with a front carriage beginning to retract, opening the side aperture and beginning to switch to supplying vacuum to the probe cannula.

In FIG. 25, the front carriage 134 has begun to proximally retract while the aft carriage 136 remains at its proximal most position. The cutter tube 36 retracts exposing a portion of the side aperture 20 of the probe cannula 22 while the vacuum and air valves 307, 351 remain in the same state with the probe cannula 22 vented to the atmosphere.

Figure 26:
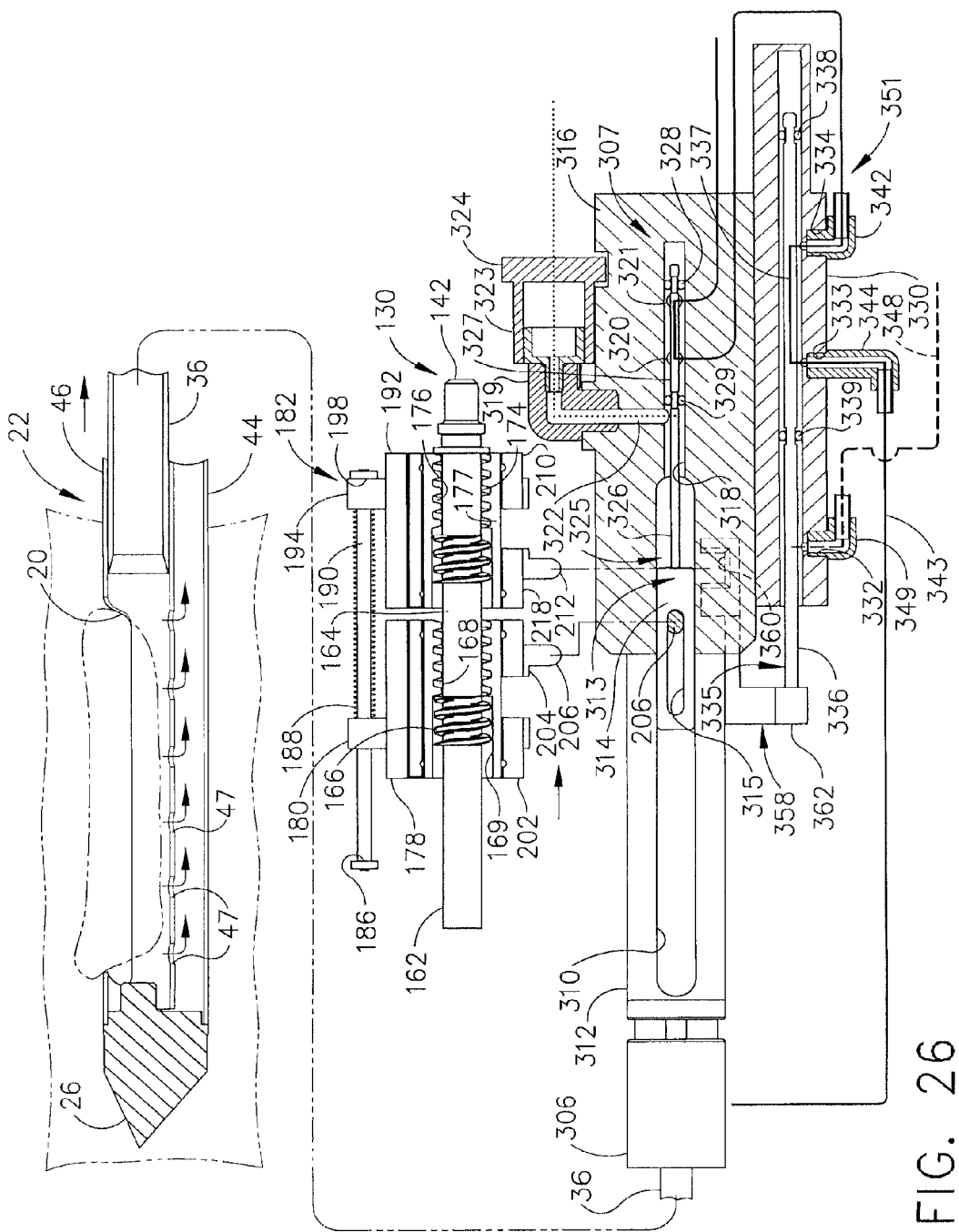
FIG. 26 is a diagrammatic view of the hand-held distal portion of the disposable probe assembly of FIG. 1 with both carriages retracted supplying vacuum pressure to the side aperture to prolapse tissue into the probe cannula.

In FIG. 26, the front carriage 134 has reached its proximal most position, fully retracting the cutter tube 36 to expose the side aperture 20 of the probe cannula 22, which is now under vacuum pressure to prolapse tissue by having the front carriage 134 position the vacuum valve 307 to pass vacuum supply from the proximal port 321 through the center port 320 to the left central port 330 to the left distal port 332 to the lateral lumen 44, drawing air through the internal vent holes 47.

Figure 27:
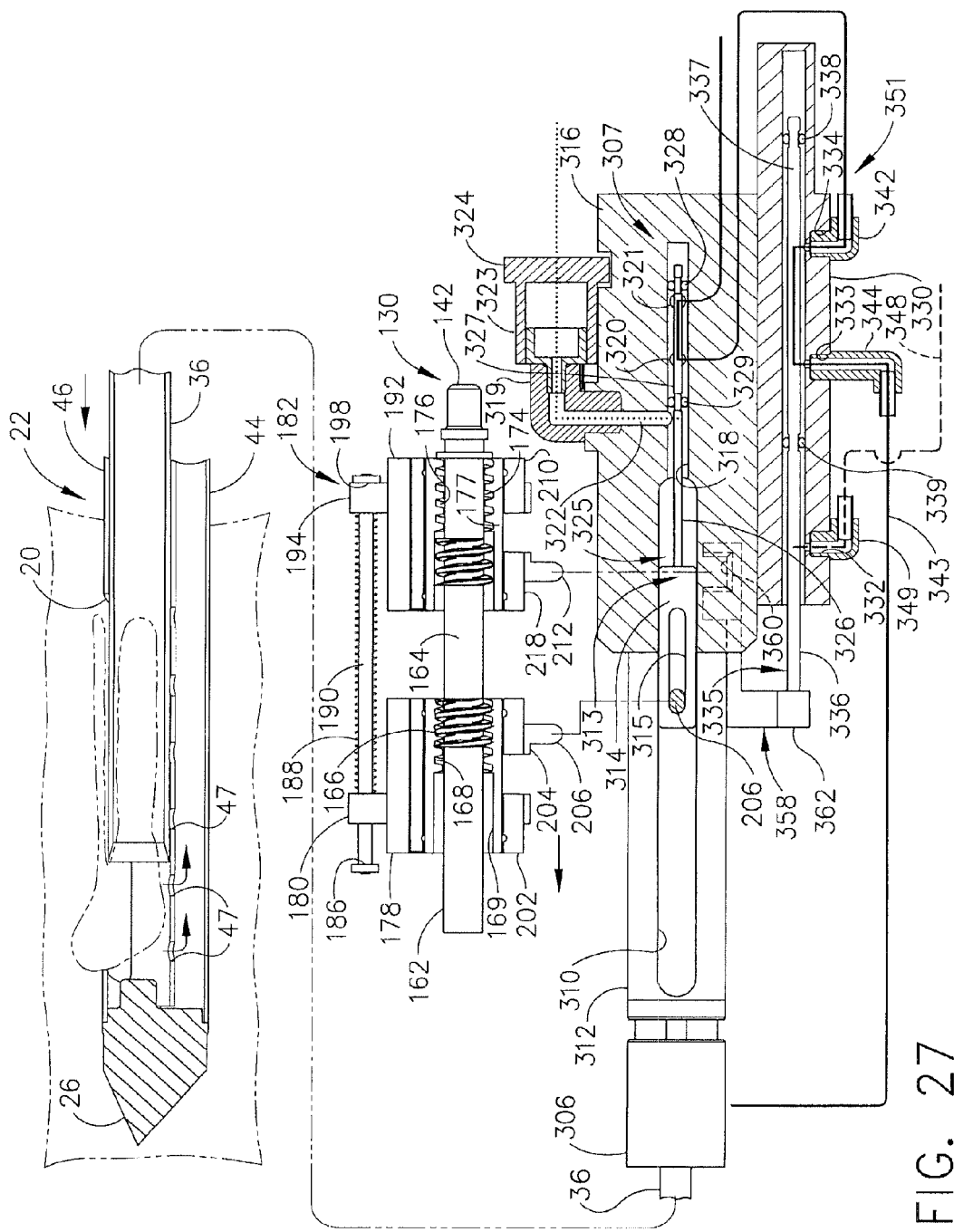
FIG. 27 is a diagrammatic view of the hand-held distal portion of the disposable probe assembly of FIG. 1 with the front carriage being distally advanced to sever tissue.

In FIG. 27, the front carriage 134 has begun to distally advance, severing tissue, while the vacuum valve 307 remains switched to vacuum supply and the air valve 351 remains in the state of passing the vacuum pressure through to the lateral lumen 44.

Figure 28:
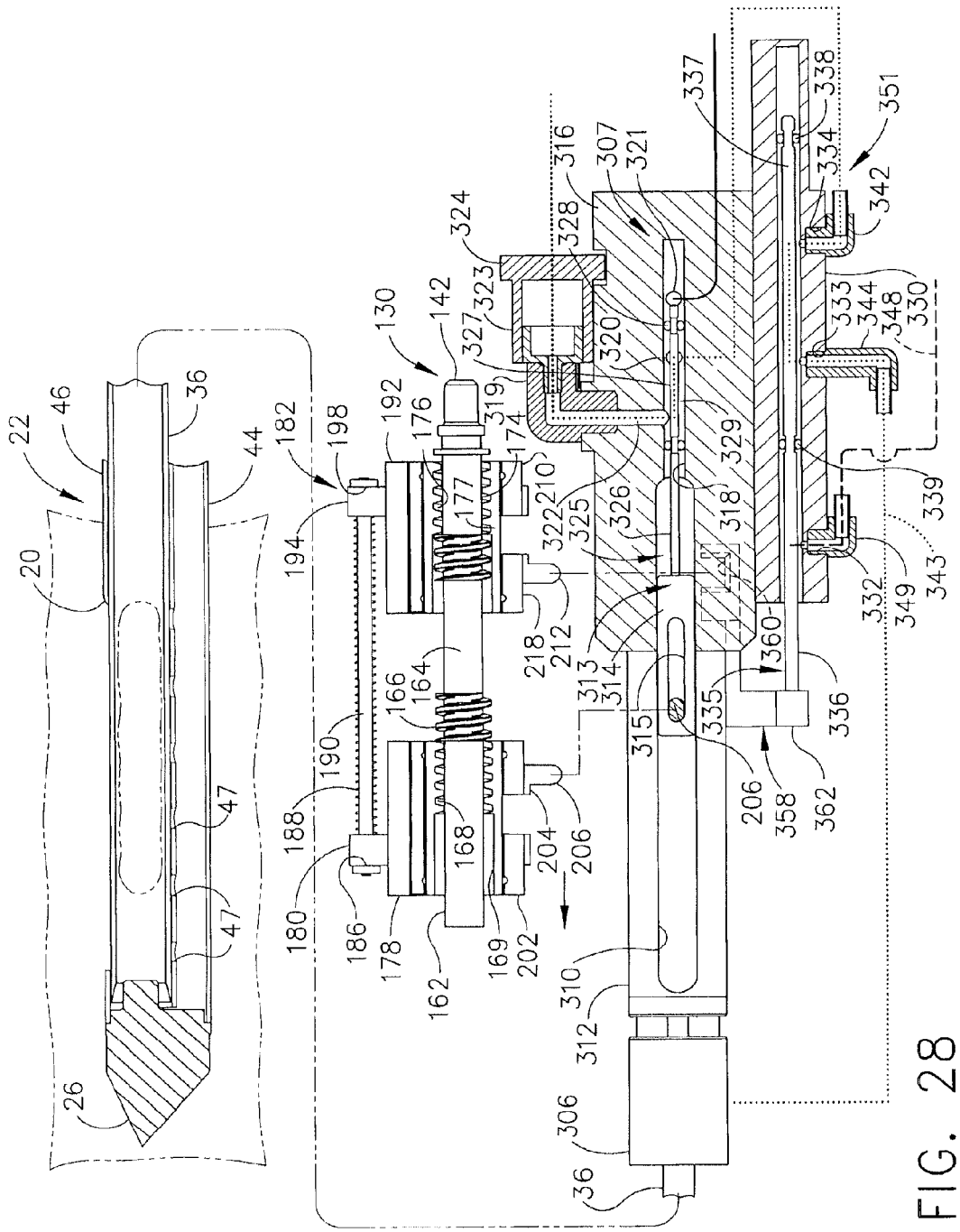
FIG. 28 is a diagrammatic view of the hand-held distal portion of the disposable probe assembly of FIG. 1 with the front carriage fully distally translated to complete severing of a tissue sample with atmosphere pressure supplied to the side aperture through a lateral lumen.

In FIG. 28, the front carriage 134 has been fully distally advanced, causing the cutter tube 36 to completely sever the prolapsed tissue into a tissue sample and switching the vacuum valve 307 to vent to the atmosphere. With the aft carriage 136 still back, the air valve 351 passes the atmospheric pressure to the lateral lumen 44 to vent the probe cannula 46.

Figure 29:
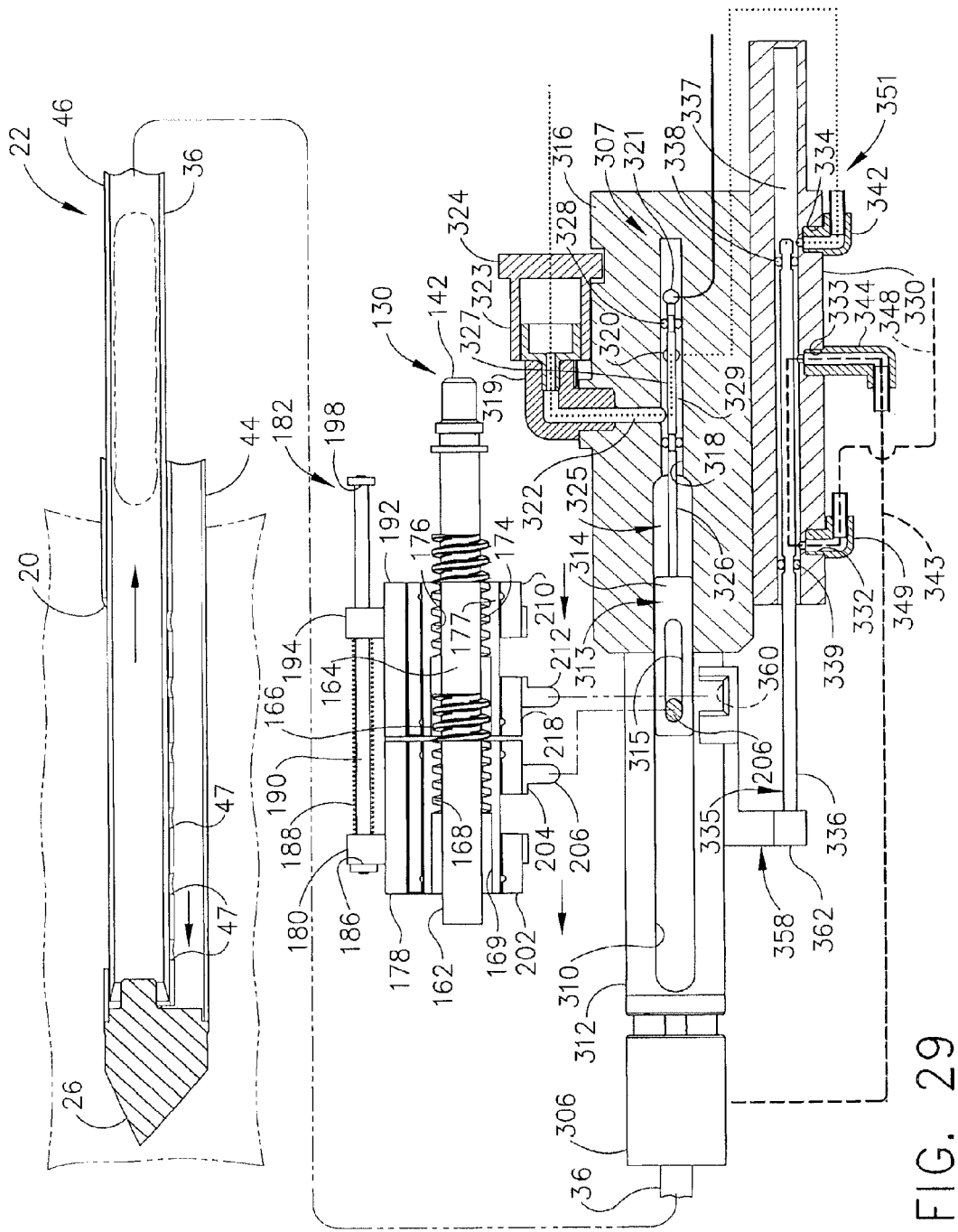
FIG. 29 is a diagrammatic view of the hand-held distal portion of the disposable probe assembly of FIG. 1 with the aft carriage distally advanced to retract the tissue sample with vacuum pressure.

In FIG. 29, the aft carriage 136 has been distally advanced, switching the air valve 351 to pass air pressure from the left distal port 332 to the left center port 333 to the lateral lumen 44. The increased air pressure passes through the holes 47 to the distal end of the cutter lumen 47 causing the tissue sample to be blown proximally back up the cutter tube 36 out of the distal hand-held portion 21 of the biopsy device 10 into the sample revolver drum assembly 18.

The clinicians benefit from being able to visually or diagnostically image the tissue samples while still being able to maintain the probe cannula 22 in tissue to take additional samples, insert therapeutic agents, deposit a marker, etc. Thus, a minimum of reinsertions and verifications of position are necessary, yet the clinician is reassured that proper samples are being taken. Moreover, avoidance of biohazards is provided by encasing the tissue samples for convenient transport for pathology assessment. Further, the individual storage allows correlating a particular sample taken at a specific position in the patient's breast. In addition, the apparatus is portable with a minimum of needed interconnections.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art, given the benefit of the present disclosure, that such embodiments are provided by way of example only. Numerous variations, changes, and substitutions will now occur to those skilled in the art without departing from the spirit and scope of the appended claims.

For example, while a rotating drum assembly provides an efficient means to capture a plurality of tissue samples, applications consistent with the present invention may include an uncircled belt that is drawn into a proximal portion of a biopsy device and then indexed to a next sample container with the filled sample containers on the belt moved out.

As another example, while automatically registering the next of a plurality of sample containers (e.g., vials) provides an efficient way of segregating tissue samples, applications consistent with the present invention may selectively uncouple the indexing of the next sample container. Instead, a manual selection may be made when the next sample container is to be positioned to receive the next sample. Alternatively, a separate control may be selected for the motor to drive the indexing arm or similar reciprocating element.

As another example, while a sample revolver drum assembly attached for movement with the proximal portions of the biopsy device has certain advantages, applications consistent with the present invention may include a revolver drum assembly coupled by flexible attachments, such as communicating a flexible drive capable for indexing motion.

As yet another example, while a detachable belt and detachable sample vials provide clinical flexibility, it should be appreciated that applications consistent with the present invention may include vials or similarly shaped sample containers that are immovably attached to a belt or a rigid outer cylinder wall structure.

As yet a further example, while a mechanical linkage is described herein for automatically indexing the samples, it should be appreciated that electromechanical positioning and control may be employed to sequencing sample storage.

What is claimed is:

1. A biopsy device, comprising:
   (a) a body;
   (b) an elongate member extending distally from the body, the elongate member having a transverse tissue receiving feature;

(c) a cutter movable relative to the elongate member to sever tissue protruding into the transverse tissue receiving feature, wherein the cutter defines a lumen, wherein the lumen of the cutter defines a first longitudinal axis; and (d) a tissue sample holder coupled with the body, wherein the tissue sample holder comprises:
(i) a housing, wherein the housing includes an annular portion,
(ii) a rotatable member having an exterior portion, wherein the exterior portion is configured to be received within the annular portion of the housing, wherein the exterior portion comprises a plurality of recesses, wherein each recess of the plurality of recesses is configured to receive a tissue sample container, and
(iii) an indexing mechanism, wherein the indexing mechanism is operable to rotate the rotatable member.

2. The biopsy device of claim 1, wherein at least a portion of the housing is transparent, wherein the indexing member is operable to selectively rotate the rotatable member such that a recess of the plurality of recesses is positioned to make a tissue sample associated with the recess is viewable via the transparent portion of the housing.

3. The biopsy device of claim 1, wherein the rotatable member defines a second longitudinal axis, wherein the second longitudinal axis is parallel to the first longitudinal axis, wherein the rotatable member is rotatable to successively index each recess relative to the lumen of the cutter.

4. The biopsy device of claim 3, wherein the indexing mechanism is operable to rotate the rotatable member about the second longitudinal axis to selectively index each recess relative to the lumen of the cutter.

5. The biopsy device of claim 4 further comprising a reusable handpiece, wherein the indexing mechanism engages with at least a portion of the handpiece, wherein the body is selectively coupleable to the handpiece.

6. The biopsy device of claim 1, wherein the rotatable member comprises an axle, wherein the axle comprises an indexing feature, wherein the indexing feature is associated with an angular position of the rotatable member relative to the body.

7. The biopsy device of claim 1, wherein each tissue sample container of the plurality of recesses is sized to receive at least one tissue sample.

8. The biopsy device of claim 1, wherein at least a portion of the housing of the tissue sample holder is transparent.

9. The biopsy device of claim 7, wherein the housing comprises a cover, wherein the cover portion is transparent.

10. The biopsy device of claim 1, wherein the cutter is slidably disposed within the elongate member, wherein the cutter is translatable and rotatable relative to the elongate member.

11. The biopsy device of claim 1 further comprising a needle tip coupled to a distal end of the elongate member.

12. The biopsy device of claim 1, wherein the plurality of recesses are equally spaced about the circumference of the rotatable member.

13. The biopsy device of claim 1, wherein the tissue sample holder is selectively coupled with the body.

14. The biopsy device of claim 1, wherein each recess of the plurality of recesses is operable to carry at least one tissue sample.

15. The biopsy device of claim 1 further comprising a sample retraction system, wherein the sample retraction system is operatively configured to move a tissue sample from the cutter into a recess of the plurality of recesses when the recess is associated with the lumen of the cutter.

16. A biopsy device comprising:
(a) a handpiece portion;
(b) a probe body detachably coupled to the handpiece portion;
(c) an elongate member extending distally from the probe body, the elongate member having a transverse tissue receiving feature;
(d) a cutter movable relative to the elongate member to sever tissue protruding into the transverse tissue receiving feature, wherein the cutter defines a lumen, wherein the lumen of the cutter defines a first longitudinal axis; and
(e) a tissue sample holder coupled with the probe body, wherein the tissue sample holder comprises:
(i) a housing, and
(ii) a rotatable member having an exterior portion, wherein the exterior portion comprises a plurality of recesses, wherein the rotatable member is receivable within the housing, wherein the rotatable member is rotatable relative to the housing, and
(iii) a plurality of tissue sample containers, wherein each tissue sample container is receivable in a respective recess of the rotatable member.

17. The biopsy device of claim 16, wherein each tissue sample container of the plurality of tissue sample containers is configured to receive at least one longitudinally oriented tissue sample.

18. The biopsy device of claim 16, wherein the rotatable member is rotatable relative to the probe body to selectively associate each recess with the lumen of the cutter.

19. The biopsy device of claim 16 further comprising an indexing mechanism, wherein the indexing mechanism is operable to rotate the rotatable member to successively index each recess relative to the lumen of the cutter.

20. A biopsy device comprising:
(a) a handpiece;
(b) an elongate member extending distally from the handpiece, the elongate member having a transverse tissue receiving feature;
(c) a cutter movable relative to the elongate member to sever tissue protruding into the transverse tissue receiving feature, wherein the cutter defines a lumen, wherein the lumen of the cutter defines a first longitudinal axis; and
(d) a tissue sample holder coupled with the handpiece, wherein the tissue sample holder comprises:
(i) a housing, and
(ii) a rotatable member insertable into the housing, wherein the rotatable member comprises a plurality of recesses, wherein each recess of the plurality of recesses comprises a face and at least one transverse open portion, wherein the rotatable member is rotatable relative to the housing about a second longitudinal axis to selectively associate each recess with the lumen of the cutter.

* * * * *